US009637753B2

(12) United States Patent
Fogher et al.

(10) Patent No.: US 9,637,753 B2
(45) Date of Patent: May 2, 2017

(54) IN-PLANT PRODUCTION OF OLIGOMERIC (COMPRISING THREE OR MORE UNITS) FORMS OF HUMAN APO A-1 PROTEIN MUTEINS

(75) Inventors: Corrado Fogher, Casalmaggiore CR (IT); Serena Reggi, Piacenza PC (IT); Kiril Perfanov, Vicomoscano CR (IT)

(73) Assignee: PLANTECHNO S.R.L., Vicomoscano (IT)

( * ) Notice: Subject to any disclaimer, the term of this patent is extended or adjusted under 35 U.S.C. 154(b) by 1629 days.

(21) Appl. No.: 12/377,085

(22) PCT Filed: Dec. 19, 2006

(86) PCT No.: PCT/IB2006/054948
§ 371 (c)(1),
(2), (4) Date: Feb. 18, 2009

(87) PCT Pub. No.: WO2008/017906
PCT Pub. Date: Feb. 14, 2008

(65) Prior Publication Data
US 2010/0168006 A1 Jul. 1, 2010

(30) Foreign Application Priority Data

Aug. 10, 2006 (IT) .............................. RM2006A0439
Dec. 7, 2006 (IT) .............................. RM2006A0661

(51) Int. Cl.
*C12N 15/82* (2006.01)
*C07K 14/775* (2006.01)

(52) U.S. Cl.
CPC ........ *C12N 15/8257* (2013.01); *C07K 14/775* (2013.01)

(58) Field of Classification Search
None
See application file for complete search history.

(56) References Cited

U.S. PATENT DOCUMENTS

| 6,258,596 B1 | 7/2001 | Benoit et al. |
| 6,617,134 B1 * | 9/2003 | Sirtori et al. ............... 435/69.7 |
| 2005/0172359 A1 * | 8/2005 | Moloney et al. ............ 800/281 |

FOREIGN PATENT DOCUMENTS

| WO | 2005/047455 | 5/2005 |
| WO | 2006/012632 | 2/2006 |

OTHER PUBLICATIONS

Scorci-Thomas et al. The effects of altered apolipoprotein A-I structure on plasma HDL concentration. (2002) Trends in Cardiovascular Medicine; vol. 12; pp. 121-128.*
Bruckert et al. The replacement of arginine by cysteine at residue 151 in Apolipoprotein A-I produces a phenotype similar to that of Apolipoprotein A-I Milano. (1997) Atherosclerosis; Bol. 128; pp. 121-128.*
Zhu et al. Cysteine mutants of human apolipoprotein A-1: a study of secondary structural and functional properties. (2005) Journal of Lipid Research; vol. 46; pp. 1303-1311.*
Savojardo et al. Improving the prediction of disulfide bonds in Eukaryotes with machine laerning methods and protein subcellular localization. (2001) Bioinformatics; vol. 27; pp. 2224-2230.*
Boehm et al. "Active expression of the ubiA gene from *E. coli* in tobacco: Influence of plant ER-specific signal peptides on the expression of a membrane-bound prenyltransferase in plant cells" *Transgenic Research*, vol. 9, No. 6, pp. 477-486, abstract only (2000).
Iturriaga et al. "Endoplasmic reticulum targeting and glycosylation of hybrid proteins in transgenic tobacco" *The Plant Cell*, vol. 1, No. 3, pp. 381-390 (1989).
Spady "Reverse cholesterol transport and atherosclerosis regression" *Circulation*, vol. 100, No. 6, pp. 576-578 (1999).
Yan et al. "Gene fusions of signal sequences with a modified β-glucuronidase gene results in retension of the β-glucuronidase protein in the secretory pathway/plasma membrane" *Plant Physiology*, vol. 115, No. 3, pp. 915-924 (1997).
International Search Report for PCT/IB2006/054948, mailed Aug. 1, 2007.
Giddings et al. "Transgenic plants as factories for biopharmaceuticals" Nature Biotechnology, vol. 18, No. 11, pp. 1151-1155 (Nov. 2000).
Nissen et al. "Effect of recombinant APOA-I milano on coronary atherosclerosis in patients with acute coronary syndromes a randomized controlled trial" Journal of the American Medical Association, vol. 290, No. 17, pp. 2292-2300 (Nov. 2003).
Stoffel et al. "Transient expression of wild type and mutant human apolipoprotein Al in COS cells" Biological Chemistry, vol. 372, No. 7, pp. 481-488 (Jul. 1991).
Von Eckardstein et al. "Structural analysis of human apolipoprotein A-I variants. Amino acid substitutions are nonrandomly distributed throughout the apolipoprotein A-I primary structure" Journal of Biological Chemistry, vol. 265, No. 15, pp. 8610-8617 (May 1990).

* cited by examiner

*Primary Examiner* — Cathy Kingdon Worley
(74) *Attorney, Agent, or Firm* — Nixon & Vanderhye PC

(57) ABSTRACT

The present invention encompasses a method for the production of Apolipoproteins in dimeric and/or oligomeric forms (comprising three or more units) of muteins of the human ApoA-1 protein in plant seeds, novel variants of these proteins having an increased stability and capacity to transport cholesterol compared to the native ApoA-1 protein, expression systems for the production thereof, plants transformed capable of producing said proteins in seeds in dimeric and/or oligomeric forms, and nutraceutical derivatives of these plants.

23 Claims, 12 Drawing Sheets

Figure 1:
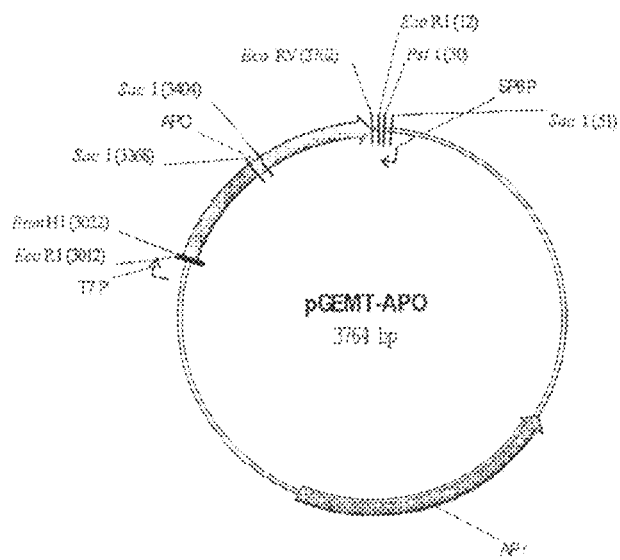

IN-PLANT PRODUCTION OF OLIGOMERIC (COMPRISING THREE OR MORE UNITS) FORMS OF HUMAN APO A-1 PROTEIN MUTEINS

This application is the U.S. national phase of International Application No. PCT/IB2006/054948, filed 19 Dec. 2006, which designated the U.S. and claims priority to Italy Application No. RM2006A000439 filed 10 Aug. 2006, and Italy Application No. RM2006A000661, filed 7 Dec. 2006, the entire contents of each of which are hereby incorporated by reference.

The present invention encompasses a method for the production of Apolipoproteins in dimeric and/or oligomeric forms (comprising three or more units) of muteins of the human ApoA-1 protein in plant seeds, novel variants of these proteins having an increased stability and capacity to transport cholesterol compared to the native ApoA-1 protein, expression systems for the production thereof, plants transformed capable of producing said proteins in seeds in dimeric and/or oligomeric forms, and nutraceutical derivatives of these plants.

STATE OF THE ART

Fats or lipids are present in our bodies in large quantities in the forms of cholesterol, triglycerides, phospholipids, and fatty acids. Lipids serve in the formation of cellular membranes, in bile acids and of certain hormones and also represent an important deposit of energy. Cholesterol, as with other fats, is not water-soluble and moves within the blood in spherical particles called lipoproteins that are constituted of some proteins as well as fats. Numerous human population studies have demonstrated that elevated levels of cholesterol (hypercholesterolemia) are associated with a higher risk of cardiovascular disease (infarct, angina, ictus), hypercholesterolemia also favours the development of atherosclerosis characterized by the presence of plaques containing cholesterol which can block arteries.

The protein components of human lipoproteins (Apolipoproteins) allows the redistribution of cholesterol from the walls of arteries to other tissues, exerting beneficial effects in the prevention of cardiovascular diseases.

Cardiovascular diseases are one of the principal causes of illness and death in industrial countries. Several factors are involved in the development of these diseases including hereditary pre-disposition, age, smoking, diet, hypertension and hyperlipidemia, in particular hypercholesterolemia. The total concentration of cholesterol in the blood is influenced by the absorption of cholesterol in the digestive tract, the synthesis of cholesterol from components of the diet and by the removal of cholesterol from the blood exerted by tissues, especially the liver; and the subsequent conversion to bile acids, steroid hormones and biliary cholesterol.

The maintenance of blood cholesterol concentration is influenced by diverse factors, both genetic and environmental. The genetic factors include the concentration of cholesterol-synthesizing enzymes, the concentration of receptors for lipoproteins in the liver, the concentration of enzymes which convert cholesterol to biliary acids, the rate of synthesis and secretion of lipoproteins, etc.

The environmental factors include diet composition, smoking, physical activity, and the use of pharmaceuticals. Within the diet variants, the concentration and types of fats, the quantity of cholesterol, and the quantity and type of fibres are the most important factors.

The relation between LDL cholesterol (Low Density Lipoprotein, considered "bad cholesterol") and HDL (High Density Lipoprotein, considered "good cholesterol") is important in determining the onset of cardiovascular diseases. The LDL lipoproteins, in fact, transport the cholesterol from the liver (where it is produced) to peripheral tissues, while the HDL lipoproteins transport the cholesterol from peripheral tissues to the liver where it is then eliminated or recycled.

Human Apolipoprotein A-1 (Seq. ID No. 56) (Apo A-1, accession n. X00566) has been the object of intense research because of its anti-atherogenic properties. The protein is found tightly associated with phospholipids to form complexes and to promote the efflux of cholesterol from cholesterol-rich cells. The maintenance of an adequate level of Apo A-1 in the blood plasma, to mitigate or to prevent the symptoms of atherosclerosis, is not simple to achieve.

The verified inverse correlation between an elevated level of HDL cholesterol in the blood and cardiovascular diseases, is attributed to the role that HDL and its major component, the Apo A-1 protein, have on Reverse Cholesterol Transport (RCT). The efficiency of RCT depends on the ability of the Apo A-1 protein to promote the efflux of cholesterol from cells, the binding of lipids, the activation of lecithin-cholesterol acetyltransferase (LCAT), and the formation of mature HDL which interacts with specific receptors and transfer proteins that eliminate cholesterol by the plasmatic flow across the liver.

It has been demonstrated that infusions of proteins such as Apo A-1 or Apo E, both recombinant or extracted, determine a reduction in the atherosclerotic burden in experimental animals.

More recent studies (Nissen et al. 2003. Effect of recombinant Apo A-1 Milano on coronary Atherosclerosis in patients with acute coronary syndromes. JAMA 290:2292-2300) indicate that the 'HDL Therapy' with infusions of a formulation (ETC-216: synthetic HDL phospholipids complex) of Apo A-1 Milano, a spontaneous variant with increased lipid-binding capacity, in its dimeric form, significantly reduces coronary atherosclerotic plaques.

The Apo A-1 Milano variant is capable of forming dimers that assemble, to form HDL particles, with the same efficiency of Apo A-1 (Calabresi et al. 1997. Biochemistry 36:12428-33). However, Apo A-1 Milano dimers, stimulate the efflux of cholesterol in a more efficient manner than HDL containing Apo A-1, are less reactive as a substrate for the enzyme LCAT, are eliminated from the circle at a lower rate, and are capable of inhibiting the estherification of cholesterol (Sirtori at al. 1999. Atherosclerosis 142:29-40).

Also the protein Apo A-1 associates and normally forms modest quantities of dimers, trimers, and quadrimers which produce particles of HDL in variable dimensions.

The presence of a cysteine residue in position 173 (Apo A-1 Milano), allows the formation of dimers as a consequence of the formation of disulfide bonds which determine an increase in the protein stability (Franceschini et al. 1990. J. Biol. Chem. 265:12224-12231) and a greater interaction with lipids and with the enzyme LCAT, thereby increasing the therapeutic effect of the protein (Chiesa et al. 2002. Circ. Res. 90:974-980).

Although the therapeutic effects of apolipoproteins have been proven, there are numerous difficulties in the preparation of pharmaceuticals which contain them. These problems can influence the type of pharmaceutical and actual usable dosage. One of such problems is a consequence of the extremely high costs of production of recombinant apolipoproteins. The production of dimers of apolipoproteins, which are more effective from the therapeutic point of view, is obtained in the art, or by purification of the dimers from plasma with all of the inherent risk and problems that purification of human blood involves, or by purification of monomers from *E. Coli*, as described in U.S. Pat. No. 6,617,134, and subsequent dimerisation of the same, which is a long, expensive procedure that is not without risk, as later explained. To summarise the current heterologous production systems for apolipoproteins are not only extremely expensive, but do even not allow the direct synthesis of the dimeric form of the protein which, as previously mentioned, is much more efficient than the monomer. The dimer is synthesized from purified monomers. This problem is reflected in practical terms by the fact that the only useable pharmaceutical are those that permits a limited amount of dosage and are administered by infusion. The reason for which only infusion pharmaceuticals can be used so far is tied to the cost of production consequently, the choice of administration by infusion is due to the fact to having to maximise, with the same production costs, the concentration of the product in the blood flow.

The administration of apolipoprotein by infusion has been shown to be extremely efficient (Nissen et al. 2003. JAMA 290:2292-2300), but it is difficult to apply such therapy protocols over long time periods, for the reasons cited above. Oral administration would require quantities of the protein that are not economical and feasible with the current methods of Apo A-1 production. This type of administration however, appears twice interesting because it has been shown that the presence and the connection of apolipoproteins on the edge of the membranes of brush cells inhibits the protein-mediated uptake of free and esterified cholesterol (Boffelli et al. 1997. FEBS Letters 411:7-11). One possible alternative suggested by the present state of the art is the oral administration of synthetic peptides that mimic the activity of the whole protein (U.S. Pat. No. 6,933,279), however, it has been demonstrated in the art that the whole protein has a greater effect than synthesised peptides.

The therapeutic use of apolipoproteins, is therefore limited by the lack of for the preparation of the protein in a sufficient quantity and in a form suitable for administration. In particular, the production of Apo A-1 with recombinant methods has been shown to be very difficult due to its amphiphilic character, for its autoaggregation and degradation (Schmidt, H. H. et al. 1997, Protein Expr. Purif. 10: 226-236).

Presently, recombinant human Apo A-1 has been expressed besides *E. coli*, in three eukaryotic systems: Baculovirus transfected *Spodoptera frugiperda* cells, stably transfected Chinese hamster ovary (CHO) cells, and in the yeast *Pichia pastoris*.

The first two systems require a long process of screening to produce and maintain the cell lines, while the production in *Pichia* yields the secretion of an altered protein with a smaller molecular weight.

Although, patent USA 20050172359 claims the production of apolipoproteins in plants and in seeds in general, describes a method of production of said proteins in which the production in seeds occurs mainly in oil bodies and in the monomeric form, as disclosed in the major part of the examples. The method of production described assumes therefore, that the monomeric, protein produced is refined from the oil bodies of the seed, where it accumulated in specific manner, in order to obtain it in pure form. However, considering the features of the said protein its purification from oil bodies would be difficult and inefficient.

The production in bacterial systems although being of interest for their capacity to produce high quantities of recombinant proteins, according to reports in the art, presents problems with the presence of undesirable affinity signals for the purification purpose. It is also known that the endotoxins of *E. coli* form strong complexes with apolipoproteins. The elimination of these toxins for pharmaceutical products is essential and technically possible, but requires complex and costly methods (U.S. Pat. No. 6,506,879) without eliminating completely the risk bound to said endotoxins.

A system of production at a low cost in expression systems not dangerous for humans which easily produces the proteins in dimeric or multimeric forms (considering the advantages of these forms listed above) would therefore allow the production of said proteins in a more efficient therapeutic form, to increase the dosage of the purified product administered in the classic manner, by means of infusion, or to further carry out other therapeutic approaches directed at increasing the plasma level of HDL cholesterol, for example by means of oral administration of apolipoproteins also introduced in a food matrix and eventually protected from degradation in the digestive tract.

SUMMARY OF THE INVENTION

The generation of recombinant plants containing a heterologous gene of interest, and their utilisation in procedures of production on an industrial scale, overcomes a series of difficulties which characterise current systems of production and in particular, those based on cell cultures.

DNA recombinant technology has allowed the generation of transgenic cells that can be used for the production of heterologous proteins of interest. In particular, animal cell cultures, in particular of mammals, allows the production of proteins of interest; but the related procedure is extremely expensive and the production of sufficient quantities for pharmaceutical use can be so uneconomic to thus limit, as it occurs at present, the possible types of administration. A solution was sought in the transformation of complex eukaryotic systems in order to guarantee the production of active proteins by economical procedures. Plants, in particular, have the necessary potential and their capacity to function as bioreactors for the production of proteins in an economical manner, and with a high yield, as has been scientifically demonstrated many times, among others, by the authors of this patent.

The accumulation of the therapeutic protein in the edible part of the plant allows the direct administration of the product, considerably lowering the cost of therapy, and allowing higher doses of the protein. The presence of apolipoproteins in the diet also facilitates also the interaction of the same with the cholesterol present in food, thus reducing cholesterol absorption.

In the present invention it has been surprisingly found that, the direction of the expression of apolipoproteins capable of forming dimers or multimers in seed specific tissues using suitable promoters and constructing suitable vectors, said apolipoproteins are expressed in seeds in high quantities, equal or higher than the 0.5% of seed storage proteins and predominantly in the dimeric or oligomeric form (≥85%).

In the state of the art, the production of the dimeric form of the Apo A-1 Milano (Seq ID No. 2) in the leaves or seeds of plants has never been demonstrated.

In the present invention has been also discovered that the introduction of mutations in specific sites of the human apolipoprotein A-1 it allows to obtain molecules able to form dimers, oligomers or even polymers. It has been surprisingly discovered that the produced muteins could be even better than the mutein Apo A-1 Milano from a therapeutic point of view, since some mutations that produce proteins able to dimerise or even oligomerise confer to these oligomers or dimers advantageous characteristics also when compared to the apolipoprotein A-1 Milano that is already therapeutically superior compared to the native apolipoprotein A-1 form. Said muteins presenting a capacity of reverse cholesterol transport and a plasma half life similar or even higher to the ones of the dimer Apo A-1 Milano. Consequently muteins of the human protein Apo A-1 capable of forming dimers or oligomers showing a capacity for reverse cholesterol transport and a plasma half life comparable or even higher to the ones of the mutein Apo A-1 Milano in it's dimeric form have been selected.

The muteins of the invention comprise new muteins of the human apolipoprotein Apo A-1 able to form dimers and/or oligomers, comprising three or more monomers, characterised in that they show in their dimeric and/or oligomeric forms biological activities equal or higher than the 10% or of the 30% or of the 50% or of the 100% or of the 200% of the activities of the apolipoprotein Apo A-1 Milano in its dimeric form in the following tests:

a'. measurement of the reverse cholesterol transport capacity evaluated by calculation of the association kinetics of equal quantities of said dimer or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer.

Therefore, objects of the present invention are seed specific expression cassettes for the expression of muteins of the human apolipoprotein A-1 able to form dimers and/or oligomers comprising three or more monomers, characterised in that they show in their dimeric and/or oligomeric forms, biological activities equal or higher than the 10% or of the 30% or of the 50% or of the 100% or of the 200% of the activities shown by apolipoprotein Apo A-1 Milano in its dimeric form in the following tests:

a'. measurement of the reverse cholesterol transport capacity evaluated by calculation of the association kinetics of equal quantities of said dimer or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer.

said cassettes comprising, ordered from 5' to 3', a seed-specific promoter, a plant signaling sequence to direct said protein, across the endoplasmic reticulum into seed storage tissues, a sequence coding one of said human apolipoprotein mutein and a polyadenylation signal, vectors for the expression in plants comprising said expression cassette, plant and plant cells genetically transformed with said vectors, the method for producing said plant transforming plant cells with said vectors and regenerating plants from said transformed cells, seeds produced by said plant, the method for producing said seeds, the method for purifying the dimeric protein from said seeds, nutraceutical and/or foods containing said dimers or multimers, the use of said seeds for the purification of proteins for the use as a drug for infusions or for the preparation of nutraceuticals and/or food containing said dimers and multimers, and the use of said seeds as means of storage and conservation of apolipoproteins in dimeric or multimeric forms.

DETAILED DESCRIPTION OF THE FIGURES

FIG. 1. Shows the map of the plasmid pGEM-APO obtained by inserting the sequence SEQ ID No. 1 retro-transcribed from mRNA purified from the human liver and amplified using the forward primer PLT1002 (SEQ ID No. 53: 5'-GGATCCGATGAACC CCCCCAGAGCC-3') and reverse primer PLT1003 (SEQ ID No. 54: 5'-GATATCT-CAC TGGGTGTTGAGCTTGTAG-3').

Figure 2:
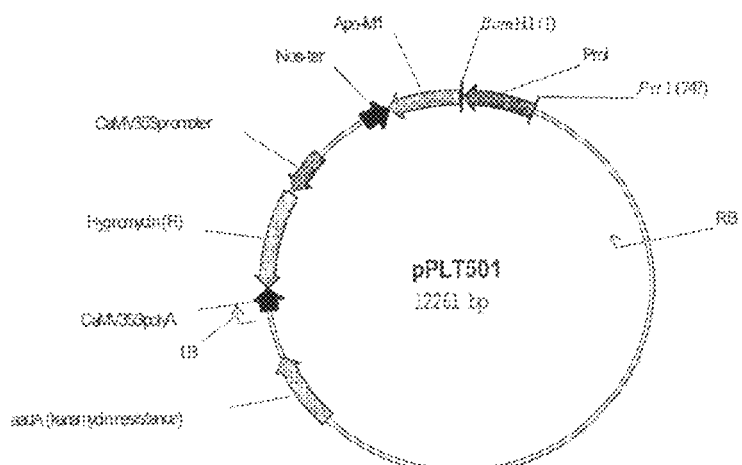

FIG. 2. Shows the map of the plasmid pPLT501 obtained by cloning into the vector pPLT500 the protein Apo A-1 mutein 1, corresponding to Apo A-1 Milano.

Figure 3:
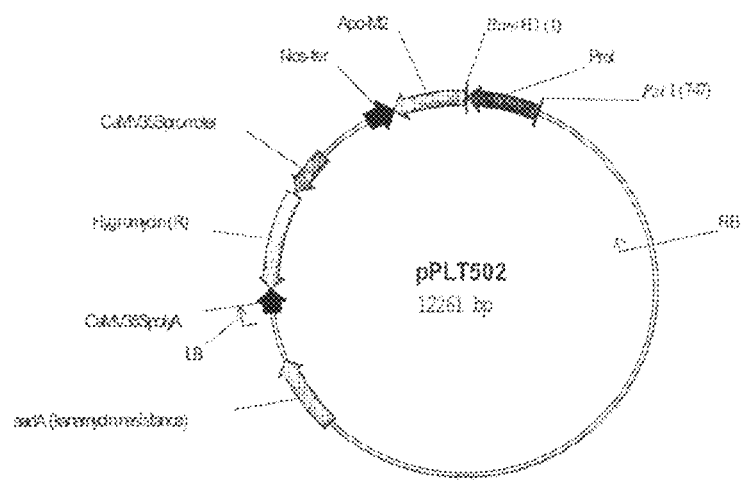

FIG. 3. Shows the map of plasmid pPLT502 obtained by cloning into the vector pPLT500 the protein Apo A-1 mutein 2.

Figure 4:
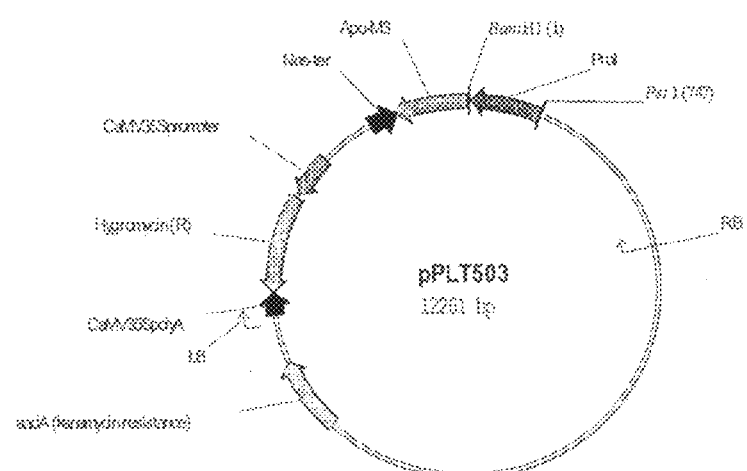

FIG. 4. Shows the map of plasmid pPLT503 obtained by cloning into vector pPLT500 the protein Apo A-1 mutein 3.

Figure 5:
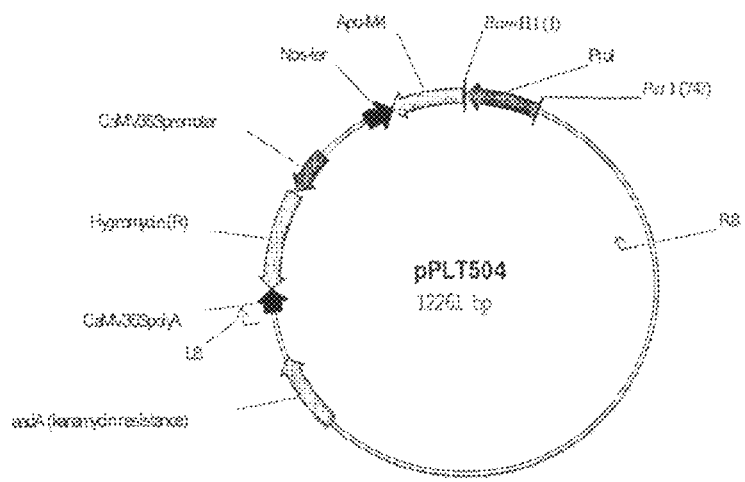

FIG. 5. Shows the map of plasmid pPLT504 obtained by cloning into the vector pPLT500 the protein Apo A-1 mutein 4.

Figure 6:
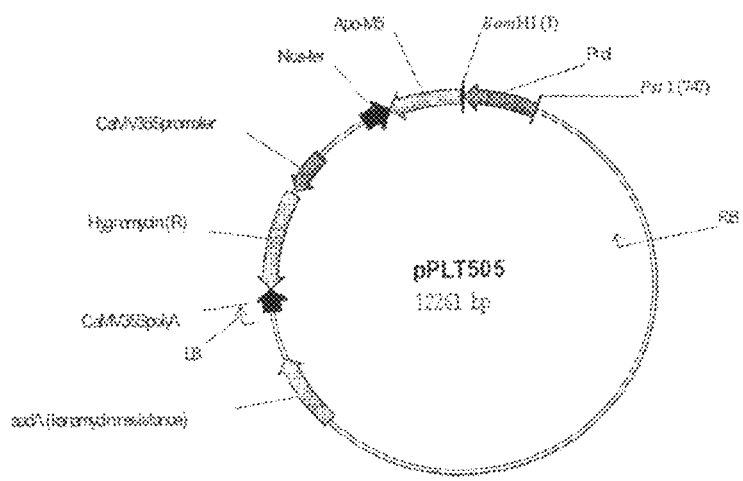

FIG. 6. Shows the map of plasmid pPLT505 obtained by cloning into the vector pPLT500 the protein Apo A-1 mutein 5.

Figure 7:
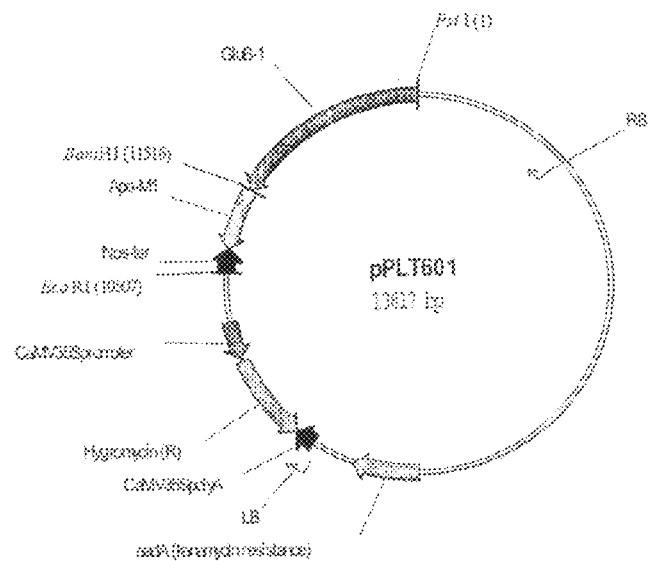

FIG. 7. Shows the map of plasmid pPLT601 obtained by cloning into the vector pPLT600 the protein Apo A-1 mutein 1.

Figure 8:
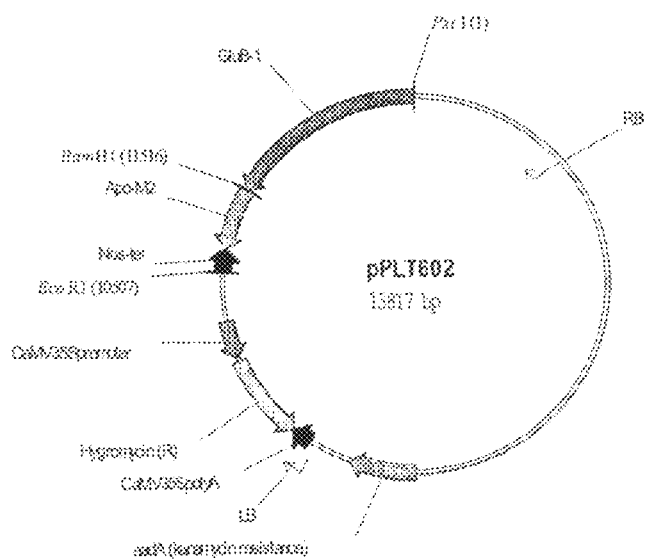

FIG. 8. Shows the map of plasmid pPLT602 obtained by cloning into the vector pPLT600 the protein Apo A-1 mutein 2.

Figure 9:
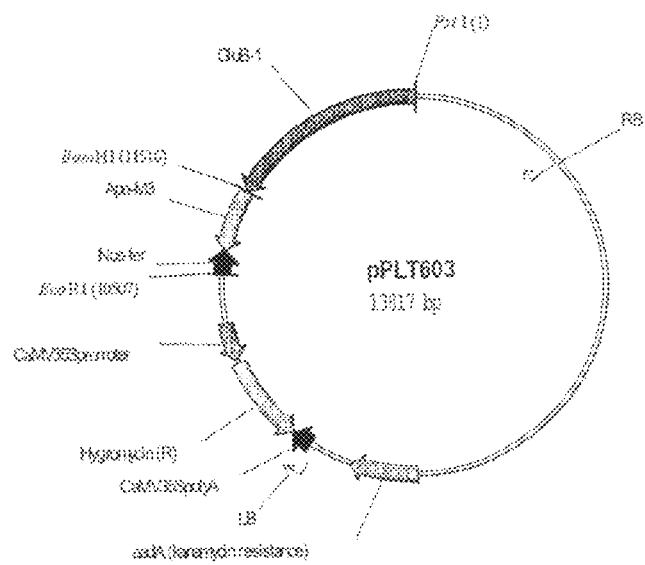

FIG. 9. Shows the map of plasmid pPLT603 obtained by cloning into the vector pPLT600 the protein Apo A-1 mutein 3.

Figure 10:
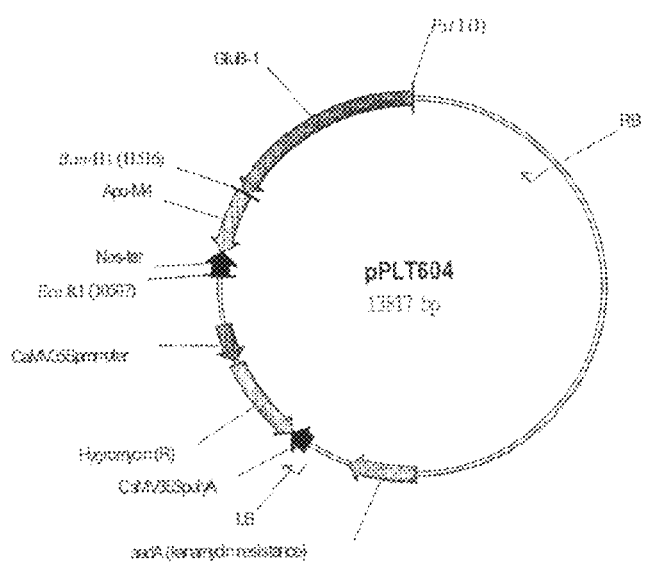

FIG. 10. Shows the map of plasmid pPLT604 obtained by cloning into the vector pPLT600 the protein Apo A-1 mutein 4.

Figure 11:
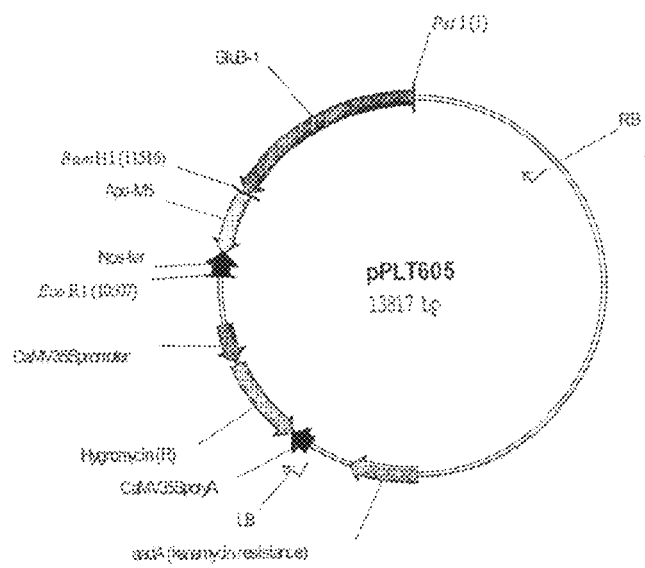

FIG. 11. Shows the map of plasmid pPLT605 obtained by cloning into the vector pPLT600 the protein Apo A-1 mutein 5.

Figure 12:
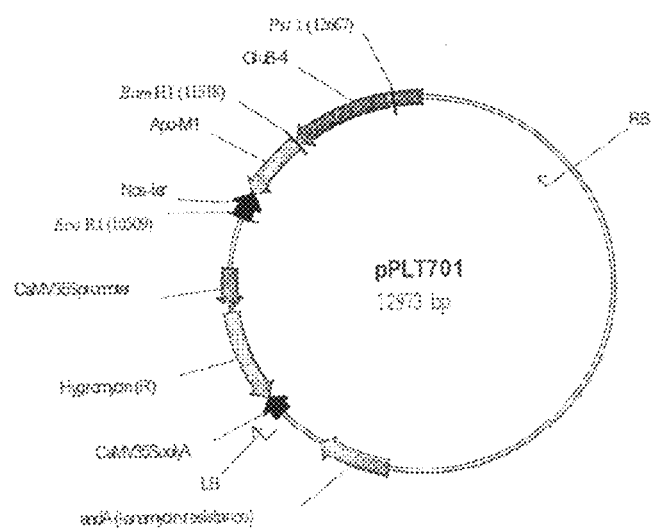

FIG. 12. Shows the map of plasmid pPLT701 obtained by cloning into the vector pPLT700 the protein Apo A-1 mutein 1.

Figure 13:
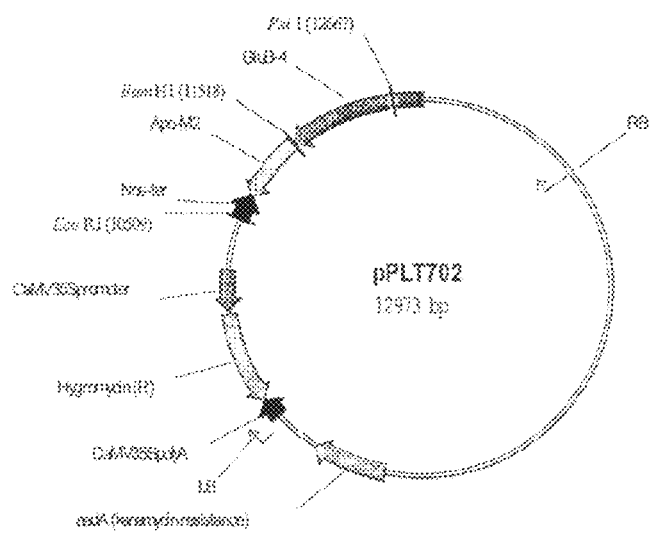

FIG. 13. Shows the map of plasmid pPLT702 obtained by cloning into the vector pPLT700 the protein Apo A-1 mutein 2.

Figure 14:
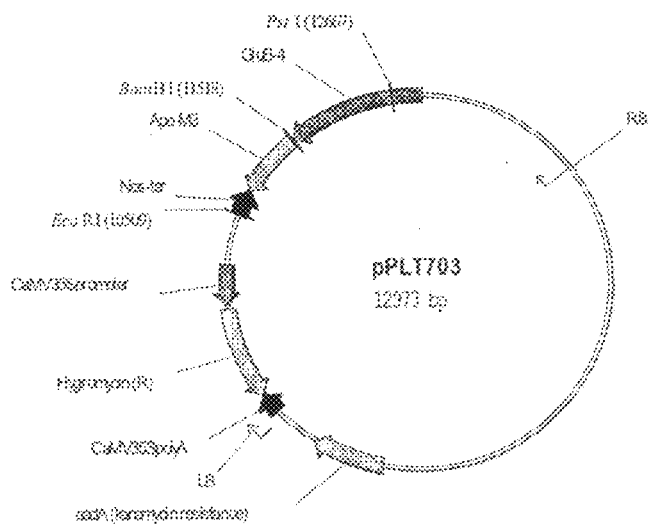

FIG. 14. Shows the map of plasmid pPLT703 obtained by cloning into the vector pPLT700 the protein Apo A-1 mutein 3.

Figure 15:
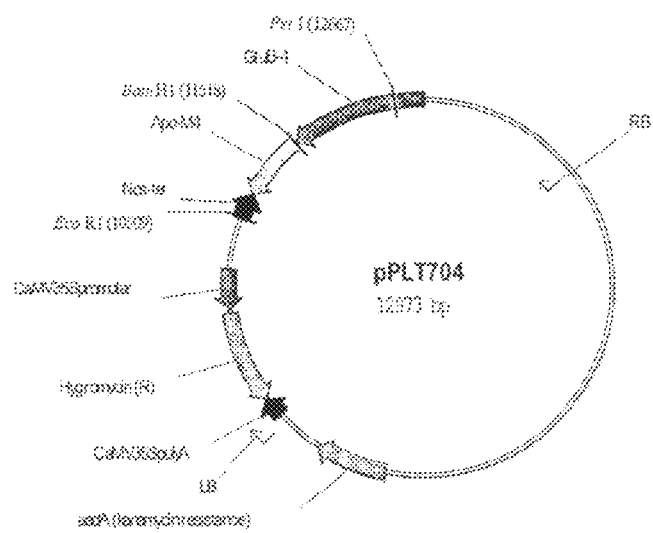

FIG. 15. Shows the map of plasmid pPLT704 obtained by cloning into the vector pPLT700 the protein Apo A-1 mutein 4.

Figure 16:
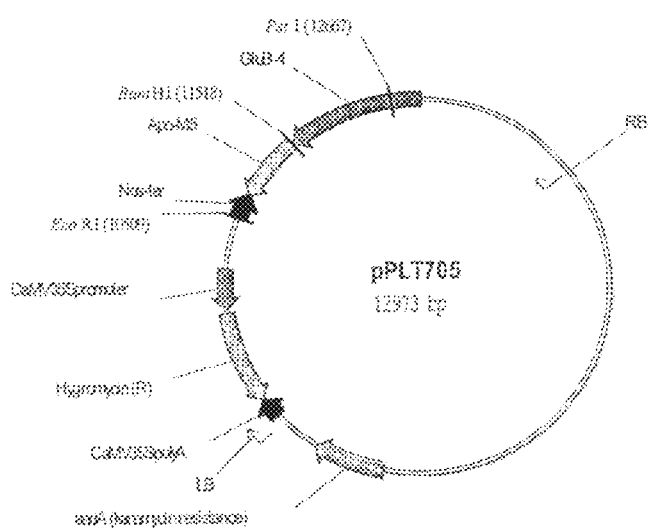

FIG. 16. Shows the map of plasmid pPLT705 obtained by cloning into the vector pPLT700 the protein Apo A-1 mutein 5.

Figure 17:
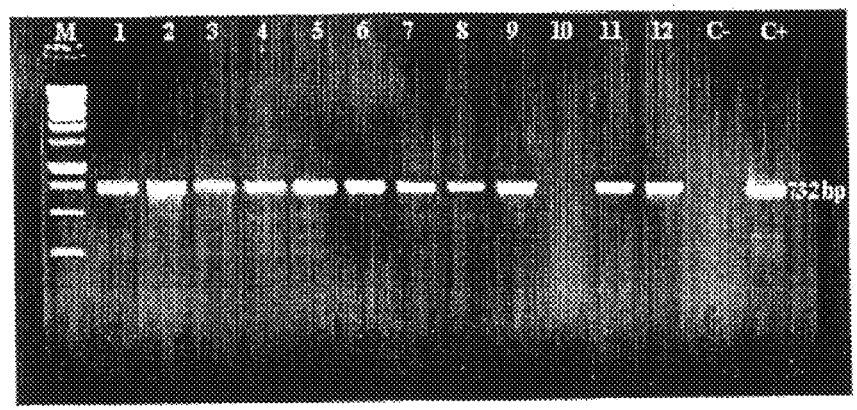

FIG. 17. Shows the result of a molecular test using the PCR technique using primers PLT1002 and PLT1003, and as template DNA extracted from leaves of $T_0$ plants to verify the presence of the mutein Apo A-1 gene. M: Molecular marker; 1-12: different lines of transgenic plants transformed with plasmids from FIGS. 2-16; C−: negative control using the rice variety Ariete; C+: positive control, plasmid pGEM-APO. The amplified band of the positive plants (1-9 and 11-12) corresponds to the expected dimensions of 732 bp.

Figure 18:
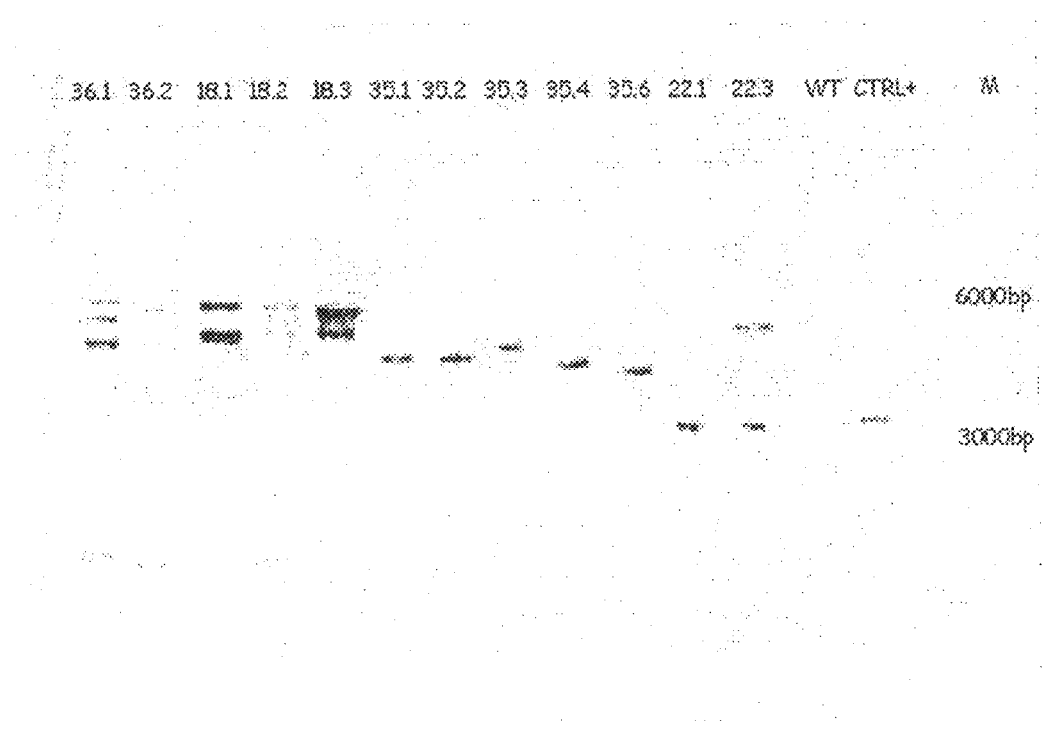

FIG. 18. Shows the result of a molecular test using the Southern technique on $T_0$ plants to verify the number of copies of the muteins Apo A-1 gene present in various transgenic lines. The plants that have a single copy of the gene are indicated by the presence of a single band (ex. Plants no. 35.1-6 and 22.1).

Figure 19:
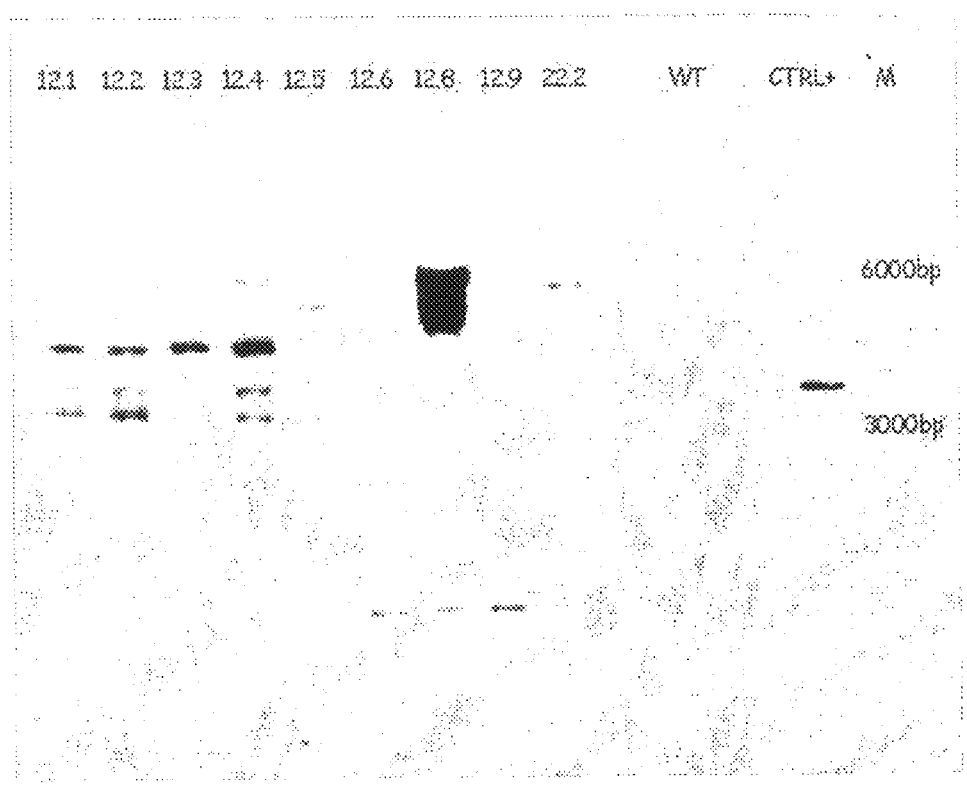

FIG. 19. Shows the result of a molecular test using the Southern technique on $T_0$ plants to verify the number of copies of the muteins Apo A-1 gene present in various transgenic lines, in addition to those presented in FIG. 18. The plants that have a single copy of the gene are indicated by the presence of a single band (ex. Plants no. 12.5, 12.6, 12.9, and 22.2).

Figure 20:
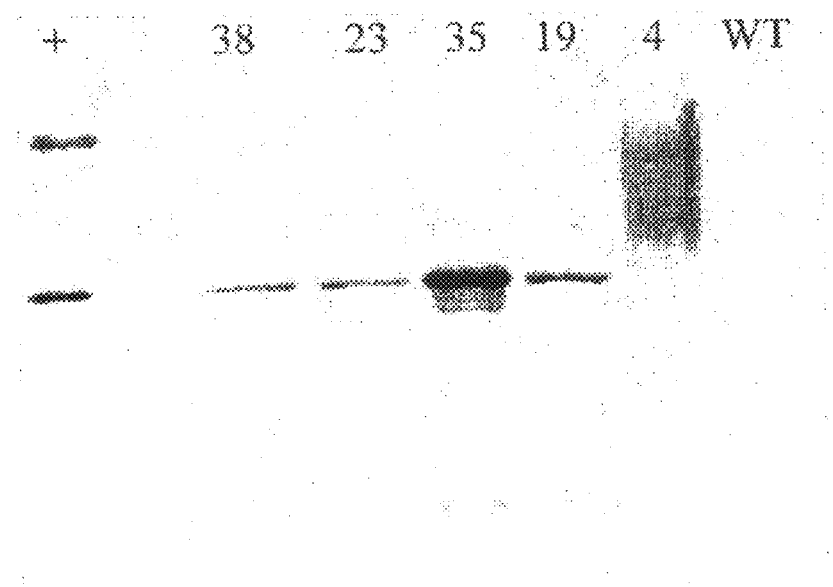

FIG. 20. Shows, the results of the Western analysis on total proteins extracted from the seeds of rice, using a buffer containing beta-mercaptoethanol, after SDS-PAGE, electroblotting and using as a primary antibody an anti-Apo A-1 obtained from goat (R1029P, Acris Antibodies, Germany) and as a secondary antibody, an anti-IgG of goat conjugated with peroxidase (Sigma) and detection using the ECL kit (Amersham). +: proteins from human serum; WT: proteins from wild type rice; 38, 23, 35, 19, 4: different transgenic lines of rice transformed with one of the plasmids from the series pPLT500, pPLT600, or pPLT700. The lower band in the positive control (+) corresponds to the monomer of Apo A-1 of about 28,000 Da.

Figure 21:
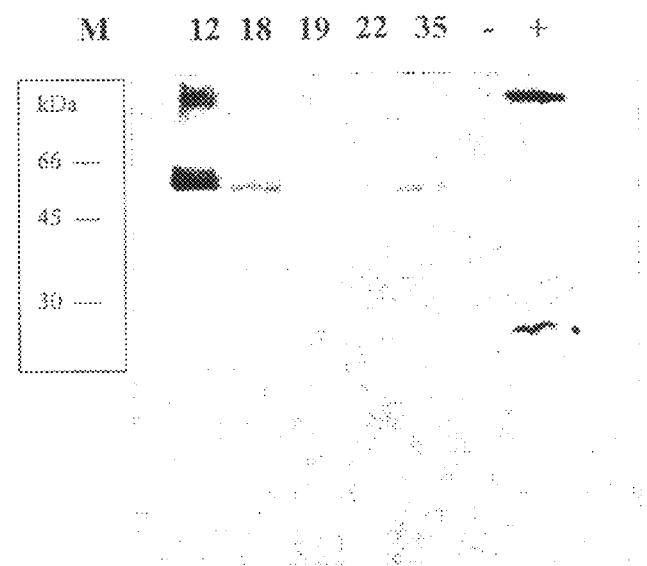

FIG. 21. Shows the result of Western assays on total protein extracted from the seeds of rice using a buffer without the reducing agent (beta-mercaptoethanol) after SDS-PAGE, electroblotting and then using as a primary antibody an anti-Apo A-1 obtained from goat and as a secondary antibody, an anti-IgG of goat conjugated with peroxidase and assayed using the ECL kit. +: protein from human serum from a person without mutations of the gene Apo A-1; −: proteins from wild type rice; 12, 18, 19, 22, 35: different transgenic lines of rice transformed with one of the plasmids from the series pPLT500, pPLT600, or pPLT700. The lower band in the control (+) corresponds to the monomer of Apo A-1 of about 28,000 Da, while the upper band present in some of the rice lines corresponds to the dimer of about 56,000 Da.

Figure 22:
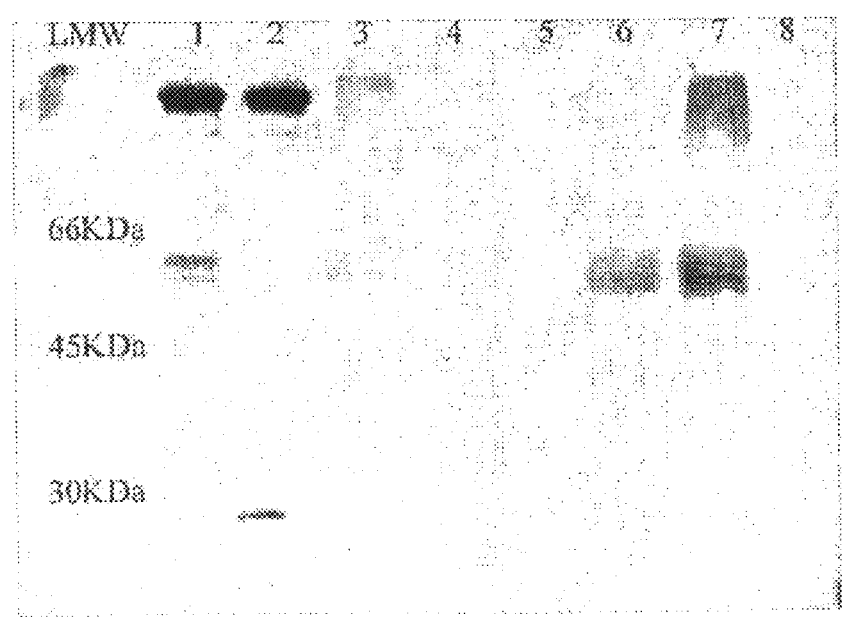

FIG. 22. Shows, the result of Western assays on the total protein extracted from the seeds of rice and human serum using a buffer without the reducing agent (beta-mercaptoethanol) after SDS-PAGE, electroblotting and the using as a primary antibody an anti-Apo A-1 obtained from goat and as a secondary antibody, an anti-IgG of goat conjugated with peroxidase and assayed using the ECL kit. 1: proteins from human serum from a person with the mutation of the gene Apo A-1 Milano, 2: proteins from human serum from a person without the Milano mutation of the Apo A-1 gene; 3-7: some lines of transgenic rice transformed with one of the plasmids of the series pPLT500; 8: proteins from wild-type rice. The lower band in the positive control n. 2 corresponds to the monomer Apo A-1 at about 28,000 Da, while the middle band in control n. 1 corresponds to the dimer at about 56,000 Da. The transgenic rice lines 3, 6, and 7 contain the protein Apo A-1 Milano primarily in the dimeric, form.

Figure 23:
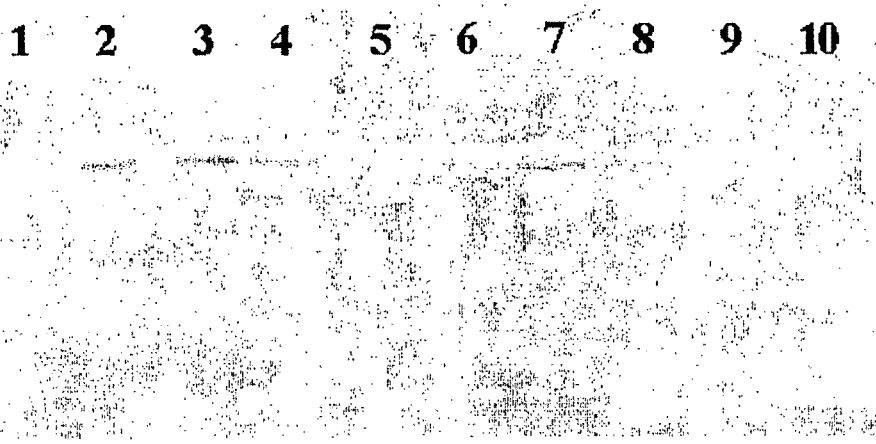

FIG. 23. Shows, the results of the Western analysis using the total proteins extracted from rice milk obtained using the procedure from example 7. 1. Sample of proteins extracted at time 0; 2. Sample of proteins extracted at time 1; 3. Sample of proteins extracted at time 2; 4. Sample of proteins extracted at time 3; 5. Sample of proteins extracted at time 4; 6. Sample of proteins extracted at time 5; 7. Sample of proteins extracted at time 6; 8. Sample of proteins extracted at time 7; 9. Sample of proteins extracted at time 8; 10. Sample of proteins extracted at time 9. The noticed band, using the technique described in FIG. 21, corresponds to the protein Apo A-1 Milano in the dimeric form.

DETAILED DESCRIPTION OF THE INVENTION

The present invention therefore relates to expression cassettes capable of directing in plant seeds the synthesis of heterologous apolipoproteins wherein said apolipoproteins accumulate primarily in the dimeric and/or multimeric forms.

The expression cassette, according to the present invention, is comprises a promoter of a plant gene specific for the expression in storage organs in the seeds. A suitable promoter, for the carrying out of the present invention, is the prolamine promoter of rice, pPROL (accession number AF156714), described in the patent PCT/ITB2003/05092, or the glutelin promoter of rice pGluB-1 (accession number AY427569), or pGluB-4 (accession number AY427571) described in Quing and Takawa 2004, Plant Biotech. J. 2:113-115, for expression in cereals, or the soybean 7s basic globulin, or the beta-conglycinin promoter of soybean described in patent WO00/04146, for the expression in plants belonging to the leguminous and solanaceae families. The promoters of glutelin, described above, are particularly advantageous for the expression in all those seeds such as rice, barley, spelt wheat, etc. that undergo industrial dehusking, because they direct the expression of the protein in a diffuse manner throughout all the endosperm of the seed. Consequently, the dehusking procedures and subsequent whitening of the seeds, which eliminate the aleuronic part and part of the external endosperm, do not result in a significant loss of recombinant protein expressed in the seed. Further, the accumulation in the seed endosperma, due to the use of said promoters, determines a simplified procedure of purification of the protein because with the whitening procedure several protein contaminants that are in the seed are eliminated.

The expression cassette, according to the present invention, also comprises a DNA sequence coding for the signal sequence of a plant protein which directs the protein of interest to the storage organs of the seed and insures, as a consequence of the protein's passage across the endoplasmic reticulum and for the oxidizing conditions (redox) of the compartment together with the presence of the disulphide isomerase enzyme, the accumulation of the protein in the dimeric, multimeric, or superior oligomeric form, depending on the number of cysteines present in the mutated protein.

A signal sequence suitable for the carrying out of the present invention is the signal sequence of the rice prolamine gene (accession number AF156714) or of the glutelin genes from rice (Accession n. AY427569 or AY427571), or of the globulin and beta-conglycinin genes of soybean (patent WO00/04146).

The expression cassette, according to the present invention, also comprises a DNA sequence coding for a gene for a human apolipoprotein A-1 capable of forming dimers and/or oligomers comprising three or more monomers, characterised in that they show in their dimeric and/or oligomeric forms, biological activities equal or higher than the 10% or of the 30% or of the 50% or of the 100% or of the 200% of the activities shown by apolipoprotein Apo A-1 Milano in its dimeric form in the following tests:

a'. measurement of the reverse cholesterol transport capacity evaluated by calculation of the association kinetics of equal quantities of said dimer or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer.

For the carrying out of the invention the cassette of the invention may contain, for example, a sequence selected from the group of sequences coding muteins having SEQ ID No. 2, 4, 6, 8, 10, 12, 14, 16, 18, 20, 22, 24, 26, 28; 30, 32, 34, 36, 38.

The above indicated muteins fulfils these characteristics and are suitable for the carrying out of the invention.

Said muteins can be obtained using all the standard techniques know by those skilled in the art. According to the present invention it is possible to carry out the replacement of amino acids in defined positions by site-directed mutagenesis. Example of muteins suitable for the carrying out of the invention are those above reported, however, the invention is not limited to them but comprises also others muteins of the human apolipoprotein A-1 not exemplified but that fulfil to the selective parameters indicated in the present description.

The functional equivalence or superiority of the dimers and/or oligomers expressed in the seeds of the invention plants when compared to the Apo A-1 Milano, can be conveniently measured with a binding test to lipids or in laboratory animals. The ability of the dimer and/or oligomer to improve the reverse cholesterol transport in a mammal can be measured verifying the lipid binding capacity, while the mutein plasma half life can be measured in test animals like rabbit or mouse.

According to the present invention these properties can be measured with the following tests:

a'. measurement of the reverse cholesterol transport capacity evaluated by calculation of the association kinetics of equal quantities of said dimer or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer.

Concerning the measure of the point a.', i.e. the check of the indicative values of the reverse cholesterol transport capacity, this can be evaluated by means of calculation of the association kinetics of the invention oligomer with dimyristoylphosphatidylcholine (DMPC) (Bergeron J. et al. 1997. Biochem. Biophys. Acta 1344:139). The DMPC is resuspended in 100 mM NaCl, 50 mM Tris-HCl pH 8.0 and 0.25 mM EDTA over is temperature of transition at a concentration of 0.5 mg/ml. The dimer or the oligomer of the invention, the buffer containing 2 mM 5'-5' dithiobisnitrobenzoate (NbS), and the DMPC suspension are incubated at 24° C. for 10 min then mixed to have a final DMPC concentration of 0.4 mg/ml and a protein concentration of 5.2 mM. The reduction of turbidity of the mix (absorbance), that reflect an increase of the lipid-protein association, is followed measuring the absorbance at 325 nm. The same test is performed in parallel with an equal molarity of the dimer of Apo A-1 Milano. As control the same tests are repeated using a reduction buffer containing 20 mM 2-mercaptoethanol or 10 mM dithiothreitol (DTT).

Concerning the measure of the point b.', the check of the indicative values of the plasma half life of said mutein, this can be evaluated in laboratory animals, for example mouse.

In an embodiment of the invention the test consist in the injection of 1 mg of the purified mutein of interest solubilised in 2 ml of the 1×PBS buffer, pH 7.4 containing dipalmitoylphosphatidylcholine (DPPC) at 8 mg/ml. The blood samples collected after the injection (time 0), after 6 hours (time 1), after 12 hours (time 2), after 24 hours (time 3), after 48 hours (time 4) and after 72 hours (time 5) are evaluated for the plasma concentration of the mutein using a quantitative ELISA, using, by way of example, a kit developed by a firm specialised in ELISA systems (InCura).

The method utilises a competitive ELISA technique with a polyclonal antibody produced in rabbit and specific for the human Apo A-1 and the followed protocol is the classical protocol used for this type of ELISA.

The standard curve, for the calculation of the antigen concentration in the plasma, is performed using the purified Apo A-1 Milano dimer at the concentrations of 0, 1, 2, 4, 8, 16 and 32 mg per ml.

In the present invention, three or more monomers means trimers tetramers, pentamers, examers up to complex oligomers or polymers. The possibility to form dimers is due to mutations who lead to the presence of at least one cysteine (1C) in the apolipoprotein Apo A-1 mutein chain. The presence of one cysteine allows the formation of a disulfide bridge and consequently the dimerisation of the molecule even in a different point of that of the Apo A-1 Milano. The possibility to form trimers is due to mutations who determine the presence of at least two cysteines (2C) in the mutein apolipoprotein Apo A-1 chain. For the formation of trimers will be necessary to combine molecules 1C and 2C in an adequate stoichiometric ratio. When at least two cysteines per monomer will be present, it will be possible to have different combinations allowing the formation of oligomers starting from tetramers up reaching to the formation of polymers. The basic condition for the carrying out of the invention is that the muteins are selected a. for their capacity to form at least dimers, b. by the fact that the dimers and the oligomers formed from the muteins of the invention keep the above mentioned fundamental properties of the dimer apolipoprotein A-1 Milano. The oligomers of the invention must have a reverse cholesterol transport capacity comparable or higher to the one of the mutein Apo A-1 Milano in its dimeric form. Capacity of reverse cholesterol transport comparable or higher to the one of the Apo A-1 Milano mutein in its dimeric form means a capacity to bind lipids equal or higher than the 10% or of the 30% or of the 50% or of the 100% or of the 200% of the Apo A-1 Milano dimer in the same test conditions; it is obvious that all the intermediate values between the above indicated are included in the invention and not only the punctual above mentioned values. Plasma half life comparable or higher than the one of the mutein Apo A-1 Milano in its dimeric form means that the plasma half life of the oligomers of the invention is at least two fold, three fold, four fold or even ten fold or more, compared to the dimer of Apo A-1 Milano in the same test conditions. Both parameters selected in the present invention are important, in fact, it has been observed in the present invention, that even in the case in which the lipids binding capacity of the invention molecules is a little superior at that of Apo A-1 Milano, the clinical effect can be superior for the increased plasma half life.

To the aim of the invention, therefore, other muteins of Apo A-1 can be used besides those described, provided that they, as already said, they keep the above mentioned properties and their expression in form of dimer and/or oligomer is higher or equal to the 85% of the Apo expressed mutein, preferably equal or higher than the 90%, even more preferably equal or higher than the 95%.

To the aim of the present invention any degeneration of the genetic code leading to the expression of the codified proteins in SEQ ID No. 2, 4, 6, 8, 10, 12, 14, 16, 18, 20, 22, 24, 26, 28, 30, 32, 34, 36 and 38 is comprised in the present invention. Mutations such as nucleotide or amino acid substitutions in which the substitution is conservative, that is, when the an amino acid residue is substituted with another chemically similar amino acid are also comprised. Non restrictive examples of these conservative amino acid substitutions (know to the expert in the art) are: substitution of a hydrophobic residue (Isoleucine, leucine, valine or methionine) with another hydrophobic residue, substitution of a polar residue with another polar residue having the same charge (ex. arginine with lysine; glutamic acid with aspartic acid) etcetera.

The nucleotide sequences coding for the muteins having the SEQ ID No. 2, 4, 6, 8, 10, 12, 14, 16, 18, 20, 22, 24, 26, 28, 30, 32, 34, 36 and 38 are immediately deducible from the said amino acid sequences. Given the correspondence of each codon with a specific amino acid residue, is sufficient to have the amino acid sequence to go back to any nucleotide sequence coding it. The nucleotide sequences of the present invention are therefore considered described by the description of the amino acid sequence coded by them.

It is unquestionable that an amino acid sequence per se gives all the necessary information for the knowledge of any nucleotide sequence coding it.

Anyhow, by way of example in the present invention a nucleotide sequence for each amino acid sequence is given, that is SEQ ID No. 1, 3, 5, 7, 9, 11, 13, 15, 17, 19, 21, 23, 25, 27, 29, 31, 33, 35 and 37 coding, respectively, for the muteins having SEQ ID No. 2, 4, 6, 8, 10, 12, 14, 16, 18, 20, 22, 24, 26, 28, 30, 32, 34, 36 and 38.

For example, in SEQ ID No. 1 the first codon, gat, coding for the amino acid Asp, can be obviously substituted by the gac codon, the second codon, gaa, coding for the amino acid Glu, can be substituted with the codon gag and so on, as any genetics may infer from the simple reading of the genetic code available in all genetics text books.

The nucleotide sequences herein described, hence, represent one of the many possible sequences coding for the muteins of the invention.

According to the invention, the gene for Apo A-1 and muteins thereof can be obtained using all the suitable procedures known or known by those skilled in the art. One usable procedure for the carrying out of the invention, entails the cloning of the gene for Apolipoprotein A-1, as cDNA from human tissue (ex. human liver), followed by modifications though site directed mutagenesis.

For the carrying out of the muteins having amino acid sequence the SEQ ID No. 2, 4, 6, 8, 10, 12, 14, 16, 18, 20, 22, 24, 26, 28, 30, 32, 34, 36 and 38 the mutagenesis can be carry out in a plasmid, for ex. pGEM-APO (FIG. 1), following the indications reported in the kit QuikChange™ (Stratagene) using the primer PLT1004 (SEQ ID No. 39: 5'-GACGAGCTGCGCCAGTGCTTGGCCGCGCGC-3') and PLT1005 (SEQ ID No, 40: 5'-GCGCGCGGC-CAAGCACTGGCGCAGCTCGTC-3') for the mutein 1 (SEQ ID No. 2) corresponding to the spontaneous mutation Milano constructing, as example, the plasmid pGEM-APO-M1; PLT1006 (SEQ ID No. 41: 5'-GAAGGTGGAGC-CGCTGTGC GCAGAGCTCCAAGAG-3') and PLT1007 (SEQ ID No. 42: 5'-CTCTTGGAGCTCTGCG CACAGCG-GCTCCACCTTC-3') for the Mutein 2 (SEQ ID No. 4) preparing, as example the plasmid pGEM-APO-M2; PLT1008 (SEQ ID No. 43: 5'-GCGCTCGAGGACCTCTGC CAAGGCCTGCTGCCC-3') and PLT1009 (SEQ ID No. 44: 5'-GGGCAGCAGGCCTT GGCAGAGGTCCTC-GAGCGC-3') for the Mutein 3 (SEQ ID No. 6) preparing, as example the plasmid pGEM-APO-M3; PLT1004-PLT1005 and PLT1008-PLT1009 for the Mutein 4 (SEQ ID No. 8) preparing, as example the plasmid pGEM-APO-M4; PLT1006-PLT1007 and PLT1008-PLT1009 for the Mutein 5 (SEQ ID No. 10) preparing, as example the plasmid pGEM-APO-M5; PLT1010 (SEQ ID No. 45: 5'-AGCCCCTGG GATTGTGTGAAGGACCTG) and PLT1011 (SEQ ID No. 46: 5'-CAGGTCCTTCACAC AATCCCAGGGGCT) for the mutein 6 (SEQ ID No. 12) preparing, as example, the plasmid pGEM-APO-M6; PLT1012 (SEQ ID No. 47: 5'-TTCAGCAAGCTGTGCGAACA GCTC) and PLT1013 (SEQ ID No. 48: 5'-GAGCTGTTCGCACAGCTTGCT-GAA) for the mutein 7 (SEQ ID No. 14) preparing, as example the plasmid pGEM-APO-M7; PLT1014 (SEQ ID No. 49: 5'-ACAGAGGGCCTGTGCCAAGAGATG) and PLT1015 (SEQ ID No. 50: 5'-CATCTCTTGGCACAGGC-CCTCTGT) for the mutein 8 (SEQ ID No. 16) preparing, as example the plasmid pGEM-APO-M8; PLT1016 (SEQ ID No. 51: 5'-GA GATGCGCGACTGCGCGCGCGCC) and PLT1017 (SEQ ID No. 52: 5'-GGCGCGCGC GCA-GTCGCGCATCTC) for the mutein 9 (SEQ ID No. 18) preparing, as example the plasmid pGEM-APO-M9; PLT1010-PLT1011 and PLT1008-PLT1009 for the mutein 10 (SEQ ID No. 20) preparing, as example the plasmid pGEM-APO-M10; PLT1012-PLT1013 and PLT1004-PLT1005 for the mutein 11 (SEQ ID No. 22) preparing, as example, the plasmid pGEM-APO-M11; PLT1012-PLT1013 and PLT1008-PLT1009 for the mutein 12 (SEQ ID No. 24) preparing, as example, the plasmid pGEM-APO-M12; PLT1012-PLT1013 and PLT1016-PLT1017 for the mutein 13 (SEQ ID No. 26) preparing, as example, the plasmid pGEM-APO-M13; PLT1014-PLT1015 and PLT1004-PLT1005 for the mutein 14 (SEQ ID No. 28) preparing, as example, the plasmid pGEM-APO-M14; PLT1014-PLT1015 and PLT1016-PLT1017 for the mutein 15 (SEQ ID No. 30) preparing, as example, the plasmid pGEM-APO-M15; PLT1014-PLT1015 and PLT1008-PLT1009 for the mutein 16 (SEQ ID No. 32) preparing, as example the plasmid pGEM-APO-M16; PLT1016-PLT1017 and PLT1004-PLT1005 for the mutein 17 (SEQ ID No. 34) preparing, as example, the plasmid pGEM-APO-M17; PLT1016-PLT1017 and PLT1008-PLT1009 for the mutein 18 (SEQ ID No. 36) preparing, as example, the plasmid pGEM-APO-M18; PLT1010-PLT1011 and PLT1004-PLT1005 for the mutein 19 (SEQ ID No. 38) preparing, as example, the plasmid pGEM-APO-M19.

Finally, the expression cassette of the present invention contains, a polyadenylation signal that may derive from the genes of prolamin, glutelins, or globulins mentioned above, or from the terminator of the *Agrobacterium* NOS gene.

The elements that constitute the expression cassette described above need to be functionally combined in the order listed above, in the direction 5'→3'.

The nucleotide sequence coding for the promoters, the signal sequences and the polyadenylation sequences can be combined in the invention cassette in a "mix" way i.e., promoter, signal sequence and polyadenylation sequence belonging to different genes (ex. prolamin promoter, glutelin leader and globulin polyadelynation sequence, etc.) or the regulation elements above mentioned belonging to the same gene (ex. all from the prolamin gene, all from the glutelin gene, all from the globulin gene, etc.) may be inserted in the cassette.

Optionally, the nucleotide sequence coding for the protein may be preceded by a short sequence apt to facilitate the purification of the protein dimer with an affinity column, as an example the his 6× tag, FLAG® (Sigma) or GST (Amersham).

Such expression cassette allows advantageously the expression of the desired apolipoprotein in seed storage compartments where it is synthesised in an essentially dimeric and/or multimeric form and in high quantities.

For essentially dimeric and/or oligomeric forms, it is intended that the apolipoprotein produced, will be located in the reserve tissues of seeds in the dimeric and/or oligomeric (three or more monomers) form, thanks to the formation of disulfide bonds between two cysteines present in the monomers in diverse positions depending on the mutein used, in a percentage comprised between greater than or equal to 85%, preferably greater than or equal to 90%, and more preferably greater or equal to 95%, and even more preferably greater or equal to 98%. This means that for the total apolipoprotein produced, the quantity of apolipoprotein found in the seeds of the invention in the dimeric and/or oligomeric form will be within the percentages above, or in an any one of the possible percentages included in a range of percentages between the 85% and 100%, including decimal values.

The plant transformation vector for the present invention can be any known vector suitable for the transformation of plant cells, including the *agrobacterium* method or physical methods, and for the expression of the protein product in plant cells. Said vector can be cut in more suitable restriction sites and the expression cassette according to the present invention can be inserted in it.

Vectors suitable for the transformation of plants according to the present invention include, but are not limited to, Ti plasmids from *Agrobacterium* and derivatives thereof, including binary and integration vectors, plasmids pBIB-KAN, pGA471, pEND4K, pGV3850, pMON505, pBI101, and also the vector pPLT2100 described in patent WO00/04146 or the vector pPLT100 or pPROL described in patent PCT/IB2003/05092, for the transformation with physical methods. Useful vectors in the present invention include, but are not limited to, the vectors pPLT 500, pPLT 600, and pPLT 700. These vectors are derived from plasmid pPZP (Hajdukiewicz et al. 1994. Plant Mol. Biol. 25:989-994), pBR322 (Bolivar et al. 1977. Gene 2:95-113), pVS1 (Itoh et al. 1984. Plasmid 11:206-220), pUC18 (Yanisch-Perron et al. 1985. Gene 33:103-119) and pBIB-HYG (Becker 1990. Nucl. Acid Res. 18:203), which already comprise the promoter with a leader and a terminator easily usable for the formation of expression cassettes described above, with the insertion of the structural part of the Apo A-1 gene of interest in the two unique BamH1 and SacI sites that are located between the promoter and the terminator. The plasmid pPLT500 contains as a promoter, the promoter of prolamine, pPROL with the leader of said gene, and as a terminator, the terminator of the NOS gene. The plasmid pPLT600 contains as a promoter, the promoter of glutelin GluB-1 with the leader of said gene, and as a terminator, the terminator of the NOS gene. The plasmid pPLT700 contains as a promoter, the promoter of glutelin GluB-4 with the leader of said gene, and as a terminator, the terminator of the NOS gene.

As previously indicated, the object of the invention is a plant genetically transformed with the vector of the invention capable of producing in seed the described apolipoprotein in an essentially dimeric and/or oligomeric form, in quantities of at least 0.5% of seed storage proteins, preferably of 1% of seed storage proteins.

According to the present invention the apolipoprotein in the seed will be found in dimeric and/or oligomeric form, at least 85% of preferably greater than or equal to 90%, or more preferably greater than or equal to 95% and even more preferably greater than or equal to 98% of the apolipoproteins present in the seed.

To carry out the present invention, plants with seeds which have an elevated protein content are suitable. Among these, legumes such as soybean and other legumes with similar characteristics, known to all plant experts, cereals such as rice, oats, barley, spelt, soft wheat, durum wheat, maize, and other cereals have seeds with high protein content, as well as tobacco are particularly suitable. In these plants, in fact, the protein content in the seeds is about 25-35% in legume seeds, 10-15% in cereals, and about 20% in tobacco. Of particular importance is also the lipid content that shall be minimised in order to simplify the purification of apolipoprotein when said purification is desired.

In one embodiment of the invention, the transgenic plant will be transformed with a vector containing an expression cassette according to the invention, in which at least the promoter and the leader sequence will be of the glutelins described above. As indicated above, the use of glutelin promoters allows an accumulation in the internal tissue of the seed, reducing the loss of recombinant protein in the phase of preparing the seed for purification. Their utilisation is of particular interest in all plants with edible seeds, such as rice, barley, spelt wheat, and other cereals, which undergo the processes of dehusking and whitening, as the accumulation of the protein in endosperm allows the majority of the dimer and/or oligomer product to remain intact after such processing procedures. Thus rendering these seeds particularly suitable for the production of food containing apolipoprotein or for direct consumption as a nutraceutical, or to facilitate the purification process of the protein for subsequent intravenous administration.

Another object of the present invention are the plant cells transformed with the vector of the invention as precursors of plants having the characteristics described above.

According to the invention, the method for the production of the genetically transformed plant capable of expressing in an essentially dimeric and/or oligomeric form muteins of the human apolipoprotein A-1 capable of forming dimers and/or oligomers comprising three or more monomers, characterised in that they show in their dimeric and/or oligomeric forms, biological activities equal or higher than the activities shown by apolipoprotein Apo A-1 Milano in its dimeric form in the following tests:

a'. measurement of the reverse cholesterol transport capacity evaluated by calculation of the association kinetics of equal quantities of said dimer or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer;

comprises the following steps:

i) transforming plant cells using a strain of *Agrobacterium* which is transformed with an expression vector comprising:

a. a promoter of a plant gene specific for expression in seed storage organs;

b. a DNA sequence encoding a signal sequence of a plant protein capable of directing said protein into seed storage organs through the passage in the endoplasmic reticulum;

c. a DNA sequence encoding a mutein of the human apolipoprotein Apo A1 capable of forming dimers and/or oligomers comprising three or more monomers, characterised in that they show in their dimeric and/or oligomeric forms, biological activities equal or higher than the activities shown by apolipoprotein Apo A-1 Milano in its dimeric form in the following tests:

a'. measurement of the reverse cholesterol transport capacity evaluated by calculation of the association kinetics of equal quantities of said dimer or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer;

d. a plant specific polyadenylation sequence;

ii) selecting the cells which have been successfully transformed with said expression vector and, iii) using said cells for the regeneration of transformed plants.

The transformation of the plant cells from which plants are regenerated according to the present invention may be performed using any one of the techniques known to those skilled in the art, such as the transformation of mature embryos or other plant tissues mediated by *Agrobacterium*, micro-injection of DNA directly into plant cells, electroporation of DNA into the protoplasts of plant cells, fusion of liposomes or spheroplasts, bombardment with microprojectiles or transfection of plant cells or tissues with appropriately modified plant viruses.

The invention may also be carried out transforming or transfecting plant cells modified by using recombinant vectors containing the expression cassette according to the present invention, and by selecting the cells transformed or transfected that express the protein. The transformed cells can be selected by selection markers commonly known in the state of art. The transformed plant cells are selected and induced to regenerate whole, fertile plants which capable of producing seeds expressing the apolipoprotein of interest in an essentially dimeric or oligomeric active form, following standard agricultural methods known in the specific sector. In one embodiment of the present invention, the transformation of the plant cells from which the plant is regenerated is carried out with cells of *Agrobacterium* containing the expression vector introduced after having rendered them competent by electroporation. The strain with the vector is used for transforming calli produced by mature embryos or cotyledons. The calli forming in the presence of the antibiotic used for selection are induced to form first the sprouts, and then the roots. The genetically transformed plant according to the present invention is a stable transgenic plant whose genetic information, introduced following the transformation, possibly contains a single copy of the gene and expresses it, without showing phenomena of gene silencing in successive generations.

Therefore, object of the invention are seeds produced by the plants of the invention, which as already indicated, can be legumes, cereals, or tobacco. The method of invention is not in reality limited to those types of plant, but these plants have, as already said, a high production of seed storage proteins and allow, hence, expression levels particularly interesting for the scope of this invention. Moreover, in most cases, the seeds are edible that hence can be used directly as a nutraceuticals or for the production of foods suitable to hinder an accumulation of cholesterol and all the harmful consequences of it in the human body.

Therefore, another object of the invention is the method for the production of seeds which accumulate in their storage organs one or more muteins of the invention in an essentially dimeric and/or oligomeric form, comprising the following steps:

i) transforming plant cells using a one or more expression vectors comprising each:

a. a promoter of a plant gene specific for expression in seed storage organs;

b. a DNA sequence encoding a signal sequence of a plant protein capable of directing said protein into seed storage organs through the passage in the endoplasmic reticulum;

c. a DNA sequence encoding a mutein of the human apolipoprotein Apo A1 capable of forming dimers and/or oligomers comprising three or more monomers, characterised in that they show in their dimeric and/or oligomeric forms, biological activities equal or higher than the activities shown by apolipoprotein Apo A-1 Milano in its dimeric form in the following tests:

a'. measurement of the reverse cholesterol transport capacity evaluated by calculation of the association kinetics of equal quantities of said diner or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer;

without the native signal sequence and without the native poliadenilation signal d. a plant specific polyadenylation sequence;

ii) selecting the cells which have been successfully transformed with said expression vector and, iii) using said cells for the regeneration of transformed plants capable of producing said seeds.

Another object of the invention is the method of extraction and purification of the apolipoprotein in an essentially dimeric and/or oligomeric form contained in the seeds of the invention, comprising the following steps:

a. Grinding said seeds in liquid nitrogen in the presence of an appropriate extraction buffer;

b. Centrifuging the thus obtained solution at 14,000 g per 15 min at 4° C.;

c. subjecting the supernatant to several chromatographic steps comprising a chromatography for exclusion and a ion exchange chromatography;

d. further purifying the partially purified dimer and/or oligomer by HPLC chromatography.

Objects of the invention are also the products obtainable with the above extraction method with exclusion of the Apo A-1 Milano dimer.

The appropriate extraction buffer for the carrying out of the invention can be one of any buffers suitable for the extraction of proteins from seeds known to those skilled in the art and easily available in laboratory manuals teaching the extraction of proteins from plant tissues. A non restrictive example, such extraction buffer may be constituted of: 50 mM Tris-HCl pH 7.0, 6 mM EDTA, 200 mM NaCl, 0.1% Triton X-100.

The dimer or the oligomer of the invention may be formed by more units (or monomers) of the same mutein or by units of different muteins to form therefore an etheromer.

The purification method above described, therefore, may include further steps apt to monomerise the mutein of the invention and join the obtained monomers to others monomers of the invention in order to create heteromers.

The oligomer of the invention can therefore be purified as such, hence in an oligomeric form, or, when it is desired to produce an heteromer, monomers of muteins of the invention may be purified by adding to the extraction buffer reducing agents such as mercaptoethanol or dithiothreitol or triscarbossiethyl phosphine (TCEP) and EDTA at pH 7.2 (the presence of a reducing environment will allow the separation of the produced oligomers in monomers) so that said monomers can be used as units for the construction of heteromers comprising two or more different muteins of the invention.

The muteins produced by the plants of the invention can hence be produced separately and than mixed in a stoichiometric ratio chosen for the production of the omomeric or heteromeric oligomer.

The heteromer of the invention can be also constructed producing simultaneously in the same recombinant organism more that one mutein of the invention, by co-transformation with two or more vectors as above described, or using chimaeric constructs containing coding sequences for two or more muteins of the invention or, in a simplest way in plant, obtaining cells expressing more than one mutein by crossing.

It is possible to cross homozygous plant lines for a mutein in a way to obtain progenies expressing more than one mutein of the invention and thus producing heteromers of the chosen muteins. The crosses, therefore, can be performed combining transgenic lines containing diverse muteins in all the possible combinations and fixing the lines in homozygosis by self-pollination or by diploidisation of haploid obtained via anthers culture. The obtained lines can be further crossbreed.

Plant lines in homozygous for one mutein can be crossbreed in order to obtain progenies expressing more than one protein of the invention and that can hence express heteromers of the selected proteins. The crossbreeds, hence, can be effected by combining transgenic lines containing different muteins in all the possible combinations and by fixing the homozygous lines by self breeding or by diploidisation of aploids obtained form anther coltures. The thus obtained lines can be further crossbreed.

In the case in which the production of the heteromer is carried out by mixing monomers of the muteins of the present invention, it will be necessary to purify the muteins of the invention in monomeric form and to use the purified monomers for the construction of the heteromer in the presence of oxidising agents such as, e.g., hydrogen peroxide or dithiobis-nitrobenzoate and/or the enzyme disulphide isomerase. An non limitative example of the method for the purification of monomers of the muteins of the invention include the following steps:

a. grinding the seed of the invention in liquid nitrogen in the presence of an appropriate extraction buffer;

b. centrifuging the thus obtained solution at 14,000 g per 15 min at 4° C.;

c. the supernatant is subject to several chromatographic steps comprising a chromatography for exclusion and a ion exchange chromatography;

d. further purifying the partially purified dimer and/or oligomer by HPLC chromatography;

e. diluting the dimer and/or the oligomer obtained in step c. or d. in phosphate buffer PBS (or similar buffers) at pH 7.4 in presence of a reducing agent such as, e.g., beta-mercaptoethanol at the concentration 14 mM;

f. gelfiltrating the suspension of step e. and the monomers are recovered;

g. the steps from a. to e. are repeated for different seeds containing said muteins;

h. the different monomers produced in steps from a. to f. are admixed in correct stoichiometric ratio in oxidising conditions and/or in presence of the enzyme disulfite isomerase;

i. the heteromers obtained in step h. are recovered.

The monomers of the purified protein in reducing conditions can be multimerised changing the oxidation conditions that allow the formation of cystine by formation of a disulphide bridge between two cysteines. The formation of the disulphide bridges can be aided adding oxidising agents such as, e.g., hydrogen peroxide or dithiobisnitrobenzoate and/or of the enzyme disulphide isomerase. In the multimerisation process it is possible to use single purified muteins or mixtures thereof starting from muteins with one cysteine (1C) and with two cysteine (2C). In the case of mixtures 1C and 2C changing the stoichiometric ratio of the two components is possible to obtain mostly a mixture of dimerstrimers instead of oligomers of higher ranks. The molecular weigh of the multimers can be estimated by SDS-PAGE with a concentration of polyacrilamide in the range 8-16%. During the polymerisation process an adjuvant can be added, for example a lipid.

The dimer and/or the oligomer of the mutein of human Apo A-1 of the invention extracted from the seeds can be used for the preparation of medicaments suitable for HDL therapy. It is preferable that said protein has a high concentration in the seed, i.e. between 0.5 and 1%, preferably between 0.8 and 1% of the seed storage proteins. Given the effectiveness of the dimer and/or oligomer of the invention in the reduction of atherosclerotic plaques, the seeds of the invention can be used for the preparation of medicaments for HDL therapy or as a cure for atherosclerosis. The medicament may be prepared by extraction of the dimer and/or multimer from the seeds of the invention and then by admixing it with a suitable carrier according to the administration for which it is intended. For an oral administration the medicament can also be prepared using flours, powders or milks from the seeds of the invention without the need for further purifications. The medicament prepared by using the seeds of the invention can be in liquid, powder, solid, suspension, emulsion form and can also be prepared for oral administration or for administration by infusion. As pharmaceuticals containing apolipoproteins are already known, the skilled person will know which formulations and dosages would be suitable for the preparation of medicaments using the seeds of the invention.

According to the invention the pharmaceutical compositions will comprise one or more dimer and/or oligomer of the invention in pharmaceutically effective concentrations as, e.g., 10 mg/kg of body weigh, or 50 mg/kg of body weigh, and pharmaceutically acceptable excipients such as adjuvants and additives as phospholipides, cholesterol or triglyceride.

Said pharmaceutical compositions can be carried out in the form of solutions for intravenous, intramuscular, subcutaneous injection or as composition for oral administration, therefore as suspension, as capsule, as tablet, as pill, as syrup or others suitable oral administrable forms, or could be realised for rectal administration or as nebulizable solution or aerosol.

The carrying out of such pharmaceutical compositions is know to the person skilled in the art and further indications are not required.

The seed of the invention can also be used as such for the purpose of reducing artherosclorotic plaques and to prevent their formation, and for the purpose of augmenting the levels of HDL cholesterol in the blood plasma, administering foods comprising derivatives thereof such as, e.g. soy milk, rice milk, or of other suitable seeds, cereals, flours, fruits, foods comprising said flours either as processed or after concentrating the active ingredient. The seeds of the invention are seeds from plant species already commonly used in large quantities in the food industry, therefore, further teaching is not necessary on how to use the seeds of the invention in a way to produce food or nutraceuticals containing, in an essentially dimeric and/or oligomeric form, muteins of the human Apo A-1 able to form dimers and/or oligomers comprising three or more monomers, characterised in that they show in their dimeric and/or oligomeric forms, biological activities equal or higher than the activities shown by apolipoprotein Apo A-1 Milano in its dimeric form in the following tests:

a'. measurement of the reverse cholesterol transport capacity evaluated by calculation of the association kinetics of equal quantities of said dimer or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer;

said nutraceuticals can then be used to increase the levels of HDL cholesterol in plasma and to reduce absorption of cholesterol in the intestine to fight atherosclerosis, as either or both, a curative, or a preventative.

The nutraceuticals of the invention containing in an essentially dimeric and/or oligomeric forms muteins of the human apolipoprotein A-1, capable of forming dimers and/or oligomers characterised in that they show in their dimeric and/or oligomeric forms, biological activities equal or higher than the activities shown by apolipoprotein Apo A-1 Milano in its dimeric form in the following tests:

a'. measurement of the reverse cholesterol transport capacity evaluated by calculation of the association kinetics of equal quantities of said dimer or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer;

will comprise products derived from the seeds of the invention, or may be constituted directly by said seeds to be consumed directly as a food such as legumes, rice, or other seeds.

The nutraceuticals of the invention can also be in the form of cereals, dried or puffed (or also of cereals muesli), can be food products made from flours or milk derived from said seeds, in the form of non-dairy milk (from plant sources), or derivatives thereof such as beverages, ices, puddings, non-dairy cheese (from plant sources), or other, in the form of powder or flours, pastry or pasta products, or can be in the form of fresh vegetables or their derivatives.

The person skilled in the art will not need further instruction beyond the normal processing of foods to develop the nutraceuticals from this invention.

The seeds of the invention can also be used as a storage mean for the muteins of the human apolipoprotein A-1 capable of forming dimers and/or oligomers comprising three or more monomers, characterised in that they show in their dimeric and/or oligomeric forms, biological activities equal or higher than the activities shown by apolipoprotein Apo A-1 Milano in its dimeric form in the following tests:

a'. measurement of the reverse cholesterol transport capacity evaluated by calculation of the association kinetics of equal quantities of said dimer or of said oligomer, and of the said dimer of Apo A-1 Milano with dimyristoylphosphatidylcholine (DMPC);

b'. measurement of the plasma half life of said dimer or of said oligomer by a plasma half life test in comparison to a calibration curve obtained performing the same test with the purified Apo A-1 Milano dimer;

in an essentially dimeric and/or multimeric form.

The following examples are intended to supply a more detailed description of the invention without binding to the same the claimed objects.

EXAMPLES

Example 1

Cloning of the Gene Coding for the Human Apo A-1 Protein

The gene coding for the human Apo A-1 protein is cloned using RT-PCR, from total RNA purified from the human liver according to the sequence information reported in SEQ ID No. 1. The gene has been recovered in its structural part of mature protein without the signal peptide and the poly-A site, and is cloned in pGEM-T (Promega) to form the plasmid pGEM-APO (FIG. 1). The primers for amplification (forward primer PLT1002 and reverse primer PLT1003) add to the 5' end the BamHI restriction site, and at the 3' end the EcoRV site in order to facilitate the subsequent transfer into the vectors pPLT500, pPLT600 and pPLT700.

Example 2

Obtaining the Muteins

The native gene obtained as in example 1, after checking that the sequence is identical to the one published, is mutagenised by using site-directed mutagenesis techniques, in order to change the amino acids in defined positions according to those reported in SEQ ID NO. 2, 4, 6, 8, 10, 12, 14, 16, 18, 20, 22, 24, 26, 28, 30, 32, 34, 36, 38. The mutagenesis of plasmid pGEM-APO has been performed according to the instructions in the QuikChange™ kit (Stratagene) using the primers PLT1004 (SEQ ID No. 39: 5'-GACGAGCTGCGCCAGTGCTTGGCCGCGCGC-3') and PLT1005 (SEQ ID No. 40: 5'-GCGCGCGGC-CAAGCACTGGCGCAGCTCGTC-3') for the mutein 1 corresponding to the spontaneous mutation Milano (indicated as pGEM-APO-M1); PLT1006 (SEQ ID No. 41: 5'-GAAGGTGGAGCCGCTGTGCGCAGAGCTC-CAAGAG-3') and PLT1007 (SEQ ID No. 42: 5'-CTCTTG-GAGCTCTGCGCACAGCGGCTCCACC TTC-3') for Mutein 2 (pGEM-APO-M2); PLT1008 (SEQ ID No. 43: 5'-GCGCTCGAGGA CCTCTGCCAAGGCCTGCTGCCC-3') and PLT1009 (SEQ ID No. 44: 5'-GGGCAGCA GGC-CTTGGCAGAGGTCCTCGAGCGC-3') for Mutein 3 (pGEM-APO-M3); PLT1004-PLT1005 and PLT1008-PLT1009 for Mutein 4 (pGEM-APO-M4); PLT1006-PLT1007 and PLT1008-PLT1009 for Mutein 5 (pGEM-APO-M5); PLT1010 (SEQ ID No. 45: 5'-AGCCCCTGGGATTGTGTGAAGGACCTG) and PLT1011 (SEQ ID No. 46: 5'-CAGG TCCTTCACA-CAATCCCAGGGGCT) for Mutein 6 (pGEM-APO-M6);

PLT1012 (SEQ ID No. 47: 5'-TTCAGCAAGCTGTGC-GAACAGCTC) and PLT1013 (SEQ ID No. 48: 5'-GAGCT-GTTCGCACAGCTTGCTGAA) for Mutein 7 (pGEM-APO-M7); PLT1014 (SEQ ID No. 49: 5'-ACAGAGGGCCTGTGCCAAGAGATG) and PLT1015 (SEQ ID No. 50: 5'-CATCTCTTGGCACAGGC-CCTCTGT) for Mutein 8 (pGEM-APO-M8); PLT1016 (SEQ ID No. 51: 5'-GAGATGCGCGACT-GCGCGCGCGCC) and PLT1017 (SEQ ID No. 52: 5'-GGCGCGCGCGCAGTCGCGCATCTC) for Mutein 9 (pGEM-APO-M9); PLT1010-PLT1011 and PLT1008-PLT1009 for Mutein 10 (pGEM-APO-M10); PLT1012-PLT1013 and PLT1004-PLT1005 for Mutein 11 (pGEM-APO-M11); PLT1012-PLT1013 and PLT1008-PLT1009 for Mutein 12 (pGEM-APO-M12); PLT1012-PLT1013 and PLT1016-PLT1017 for Mutein 13 (pGEM-APO-M13); PLT1014-PLT1015 and PLT1004-PLT1005 for Mutein 14 (pGEM-APO-M14); PLT1014-PLT1015 and PLT1016-PLT1017 for Mutein 15 (pGEM-APO-M15); PLT1014-PLT1015 and PLT1008-PLT1009 for Mutein 16 (pGEM-APO-M16); PLT1016-PLT1017 and PLT1004-PLT1005 for Mutein 17 (pGEM-APO-M17); PLT1016-PLT1017 and PLT1008-PLT1009 for Mutein 18 (pGEM-APO-M18); PLT1010-PLT1011 and PLT1004-PLT1005 for Mutein 19 (pGEM-APO-M19).

The mutants obtained have been checked at the sequence level, confirming the insertion of the mutation desired, and the same are reported in SEQ ID NO. 2, 4, 6, 8, 10, 12, 14, 16, 18, 20, 22, 24, 26, 28, 30, 32, 34, 36, 38.

Example 3

Preparation of the Plant Transformation Vectors

The various genetic forms corresponding to the muteins of interest have been recovered from plasmids pGEM-APO-M1, pGEM-APO-M2, pGEM-APO-M3, pGEM-APO-M4, pGEM-APO-M5, pGEM-APO-M6, pGEM-APO-M7, pGEM-APO-M8, pGEM-APO-M9, pGEM-APO-M10 pGEM-APO-M11, pGEM-APO-M12, pGEM-APO-M13, pGEM-APO-M14, pGEM-APO-M15 pGEM-APO-M16, pGEM-APO-M17, pGEM-APO-M18 and pGEM-APO-M19 by removing the APO fragment with the enzymes BamH1-EcoRV and inserting it into the BamH1 and SacI restriction sites of vectors pPLT500, pPLT600, and pPLT700, linearised by the same enzymes. Following the cloning, the resulting APO genes result under the control of the promoter and leader pPROL, acc. n. AF156714 (pPLT500) or GluB-1, acc. n. AY427569 (pPLT600) or GluB-4, acc. n. AY427571 (pPLT700) to form the plasmids pPLT501, pPLT502, pPLT503, pPLT504, pPLT505, pPLT601, pPLT602, pPLT603, pPLT604, pPLT605, pPLT701, pPLT702, pPLT703, pPLT704, pPLT705 reported by way of example in FIGS. 2-16, plus the plasmids pPLT506, pPLT507, pPLT508, pPLT509, pPLT510 pPLT511, pPLT512, pPLT513, pPLT514, pPLT515 pPLT516, pPLT517, pPLT518, pPLT519, pPLT606, pPLT607, pPLT608, pPLT609, pPLT610 pPLT611, pPLT612, pPLT613, pPLT614, pPLT615 pPLT616, pPLT617, pPLT618, pPLT619, pPLT706, pPLT707, pPLT708, pPLT709, pPLT710 pPLT711, pPLT712, pPLT713, pPLT714, pPLT715 pPLT716, pPLT717, pPLT718 and pPLT719.

All of the plasmids obtained have then been transferred into cells of the EHA105 (Hood at al. 1993. Transgenic Res. 2:208-218) strain of *A. tumefaciens*, rendered competent by electroporation. The strains containing the different plasmids have been used for the genetic transformation of rice.

Example 4

The Genetic Transformation of Rice

The genetic transformation of rice *Agrobacterium* mediated has been performed according to the protocol of Hiei at al. 1994. Plant J. 6:271-282 with minor modifications, using mature embryos from the variety Ariete.

The steps for transformation comprise of the following steps:

1. Induction of Callus

After the manual dehusking, the seeds are sterilized for 1 minute in 70% ethanol and 30 minutes in a solution of 30% commercial bleach, and then rinsed 6 times for 15 minutes with sterile distilled water. One hundred seeds have been used from which the embryos have been removed for every transformation, 10 embryos have been placed in 100 mm diameter petri plates containing 25 mL of callus induction media with agarose.

The plates closed with parafilm are maintained in the dark at 28° C. for 3 weeks. In this period the embryo germinates and forms embryogenic callus tissue on the scutellum. This callus is collected and nodules of approximately 1 mm are transferred to fresh NB media for 1-2 weeks.

2. Co-Cultivation with *Agrobacterium*

The *Agrobacterium* is cultured on plates with AB media containing suitable antibiotics according to the strain. The strain is cultivated for 3 days at 28° C. The bacteria are collected with a spatula and re-suspended in liquid media at a density of $3-5 \times 10^9$ cells/ml ($OD_{600}$ ~1) and transferred to a petri dish. The rice callus is immersed in a bacterial suspension for 10-15 minutes, then dried on sterile filter paper and subsequently transferred to a plate with agarose media for co-cultivation. The plates are closed with parafilm and left to incubate for 3 days at 25° C. in the dark.

3. Selection for the Hygromycin Resistant Calli

The calli are taken from the plate for co-cultivation and transferred to plates containing selection media I (R2). After 2 weeks on selection media, the calli are transferred to selection media II and after one week, a few resistant calli appear, white and globular on the surface of the main callus clump. The resistant calli are removed by spatula and transferred to fresh selection media II where the resistant calli grow further.

4. Regeneration of Plants

The hygromycin resistant embryogenic calli are selected and transferred to a pre-regeneration medium, incubated for one week in the dark at 28° C. and then reselected from the pre-regeneration medium and transferred to regeneration medium, max. 4-6 per plate. They are then incubated in light (fluorescent, 4000 lux) at 28° C. for 3-4 weeks. When the plants reach 3 cm, they are transferred individually into tubes (200×30 mm) containing 25 ml of rooting media and are maintained in light for 3 weeks at 28° C. When the leaves start to fold over the top of the test tube, the plants are transferred in the evening to soil in a container which maintains high humidity (85%). The containers are gradually opened over time to acclimate the plant to greenhouse conditions. The seeds of the $T_0$ plants are collected after 5 months.

Example 5

Molecular and Biochemical Characterization of the Transgenic Rice Lines

During the period before flowering, the $T_0$ plants were checked using PCR (FIG. 17) to verify the presence of the transgene. The PCR was done using as template the DNA extracted from leaves of the rice lines resistant to hygromycin, using the primers PLT1002 and PLT1003, which amplify the entire Apo A-1 gene, visualized, in the case of successful transformation, by a fragment of 932 bp. $T_0$ plants were then checked by Southern analysis to verify the copy number of the transgene present single lines transformed with independent transformation events (FIGS. 18 and 19). The total DNA extracted from the leaves of transgenic rice was cut using the enzyme XbaI and separated using electrophoresis on a 1.8% agarose gel, and transferred to a nitrocellulose membrane, which then was hybridized using the probe constituted of the gene APO marked with DIG using the kit PCRDIG Probe Synthesis (Boehringer) and CDPstar (Boehringer) detection. Results from the hybridization plants with a single copy of the gene show a single band of variable length, varying depending on the site of gene integration into the rice genome.

The seeds collected from the $T_0$ plants testing positive for the transgene were then used to verify the expression of the same using the Western Analysis (FIG. 20).

The total Apo A1 Milano proteins from rice seeds was extracted from the seeds using extraction buffer containing 50 mM Tris-HCl pH 7.0, 5 mM EDTA, 200 mM NaCl, 0.1% Triton X-100, after separation by electrophoresis in acrilamide gel, that requires admixing with a loading buffer containing 60 mM Tris pH 6.8, 25% glycerol, 2% SDS and 14.4 mM β-mercaptoethanol (the last is added only when it is desired to verify the structure of the monomer), were transferred using electroblotting (solution of 25 mM Tris, 192 mM glycine, 20% methanol, 30 V at 4° C. over night) to a nitrocellulose membrane, hybond ECL (Amersham).

The membrane with the immobilised protein was placed in a solution of TBS-T and 5% skim milk and agitated for 60 minutes, and then, after a few washes, the membrane is placed in the same solution, but which contains additionally the primary antibody in 1:5000 proportion (Anti-Apo A-1 Goat).

After the reaction with the primary antibody, the membrane was washed and then exposed to the secondary antibody (Anti-Goat peroxidase conjugate), always in the solution of TBS-T skim milk, in a proportion of 1:12,000.

After the reaction with the secondary antibody the membrane was washed several times and then placed in a solution from the ECL kit for chemiluminescence from Amersham.

The membrane was then placed in contact with photographic film (Hyperfilm MP, Amersham) in a dark room for variable times.

The most productive plants were taken forward to the $T_2$ and T3 generations in order to identify individual homozygote plants for the presence of the apolipoprotein gene and to verify the absence of the silencing phenomenon. Western analysis was conducted on the most interesting lines, for the presence of the transgene in single copy, and for the high expression thereof, has been repeated on $T_3$ seeds in non reducing conditions in order to verify the presence of the protein in the dimeric or multimeric form (FIG. 21).

Rice plants with the gene for apolipoprotein under the control of the promoters pPROL, GluB-1, GluB-4 and Globulin 7S all lead to the accumulation of a protein, reacting with antibodies specific for Apo A-1 (FIG. 20), having a molecular size of 28 kDa, in the monomeric form in the presence of the reducing agent in the extraction buffer, corresponding to the mature human protein, and in the dimeric form, about 56 kDa in the absence of the reducing agent (FIGS. 21 & 22). The presence of the recombinant protein only in the seed and not in the leaves has been verified in all of the transgenic plants examined.

Example 6

Purification of the Apo A-1 Milano Protein from Rice Seed and its Verification with Mass Spectrometry The extraction of all proteins from rice seed was performed by grinding the dehusked and whitened seeds in liquid nitrogen in the presence of an extraction buffer (0.5 M sucrose, 0.1% ascorbic acid, 0.1% cys-HCl, 0.01 M Tris-HCl, 0.05M EDTA pH 6).

The solution was centrifuged for 30 minutes at 14,000 g at 4° C., and the supernatant lyophilised.

For the verification of the molecular weight of the dimeric form by SDS-PAGE, a sample of protein extract (20 µl), before the lyophilisation or in other phases of purification, was mixed with a colorant (SDS loading buffer, without reductant) and was loaded with the sample into a mini-gel of 10% polyacrylamide. The running conditions were initially 10 mA, and then 20 mA for the rest of the run, in 1× Tris-glycine buffer. The gel was then stained with comassie blue or, for the identification of the specific recombinant protein, with an antibody anti-ApoA-1 and the molecular weight calculated in reference to molecular weight standards.

The total lyophilized proteins were de-lipidized with diethylether/ethanol (3/1, v/v) and solubilised in 0.1 M Tris-HCl, 0.04% EDTA, 0.01% $NaN_3$, 6 M guanidine HCl, pH 7.4, and passed through a Sephacryl S-300 HR column (Amersham) equilibrated with 0.1 M Tris-HCl, 0.04% EDTA, 0.01% $NaN_3$, pH 7.4, containing 4 M guanidine-HCl. The fractions corresponding to the dimer of Apo A-1 mutein were concentrated and passed through the same column a second time. The purified protein was dialyzed in 5 mM $NH_4HCO_3$ 0.01% $Na_2$-EDTA, pH 7.4, and lyophilized. The purity (≥95%) was determined using SDS-PAGE and silver staining.

One sample of the purified protein was resuspended in solvent composed of 50% acetonitrile and 0.5% formic acid. After centrifugation at 13,000 rpm the sample was injected in the capillary and the mass spectrum was determined (API I, Perkin Elmer) confirms the expected finger print of the Apo A-1 protein.

Example 7

Production of Rice Milk and Verification of the Stability of the Apo A-1 Milano Produced in Plants Rice milk was obtained from $T_3$ generation seeds from transgenic rice lines grown in greenhouses. At maturity the seeds were collected, dehusked, and whitened with a laboratory scale rice cleaner (G150/R, Colombini) The cleaned seeds were ground with a grinder using a grinding stone to obtain a flour with particles of approximately 40 micron in diameter, capable of forming a suspension in water. A 20% suspension of the flour was made in water, and the suspension was heated to 40° C. for different time periods favourable for saccharification. At the end of the saccharification, the rice milk was stored at 4° C. and the stability of the Apo A-1 Milano protein present was evaluated at intervals of one week for time 0 (end of the preparation) to time 9 (63 days). For all time periods tested, the protein was shown to be stable as demonstrated by the presence of the largest band at 56,000 Da from Westerns done after SDS-PAGE on total proteins extracted from milk. The concentration estimate of Apo A-1 Milano in the rice milk can vary between 89 to 178 mg per liter of milk, prepared as described above, and depends on the levels of expression of the transgene. The concentration of apolipoprotein can be augmented considerably, by using in place of rice flour, a total protein extract of rice, for example, from 40, 50, 60, or 70% protein.

In the case of soybean milk, the concentration of flour in suspension can be of 9%. As a substitute to the flour of soybean, it is possible to use soy protein isolate which has a protein content as high as 90%, on a wet basis, it is possible to obtain a higher concentration of recombinant protein per liter of milk.

The invention claimed is:

1. A genetically transformed plant with one or more expression vectors comprising a seed-specific expression cassette and a nucleotide sequence encoding a mutein of human apolipoprotein (Apo) A-1, expressing in the seed's storage tissue one or more of said muteins, and forming oligomers comprising three or more monomers, in an essentially oligomeric form, said one or more muteins characterised in that they show in their oligomeric forms biological activities equal to or higher than the activities shown by apolipoprotein (Apo) A-1 Milano in its dimeric form in the following tests:
   a') measurement of the reverse cholesterol transport capacity evaluated by calculation of the association kinetics of equal quantities of said oligomer, and of said dimer of Apo A-1 Milano with dimyristoylphosphatidylcholine (DMPC); and
   b') measurement of the plasma half life of said oligomer by a plasma half life test in comparison to a calibration curve obtained performing the same test with the purified Apo A-1 Milano dimer.

2. A plant according to claim 1, wherein said expression vector is a plasmid.

3. A plant according to claim 1, wherein said plant is a legume, a cereal, or tobacco.

4. A plant according to claim 2, wherein said plant is selected from the group consisting of rice, maize, hard and soft wheat, oats, spelt, barley, soybean, pea, bean, and tobacco.

5. A seed comprising in its storage organs one or more muteins of human apolipoprotein (Apo) A-1 capable of forming oligomers comprising three or more monomers, in an essentially oligomeric form; said one or more muteins characterised in that they show in their oligomeric forms biological activities equal to or higher than the activities shown by apolipoprotein (Apo) A-1 Milano in its dimeric form in the following tests:
   a') measurement of the reverse cholesterol transport capacity evaluated by calculation of the association kinetics of equal quantities of said oligomer, and of said dimer of Apo A-1 Milano with dimyristoylphosphatidylcholine (DMPC); and
   b') measurement of the plasma half life of said oligomer by a plasma half life test in comparison to a calibration curve obtained performing the same test with the purified Apo A-1 Milano dimer.

6. A seed, according to claim 5, wherein said one or more muteins are present in oligomeric form in a quantity greater than or equal to 85% of total one or more Apo A-1 muteins of the seed.

7. A seed, according to claim 6, wherein said one or more muteins represent between 0.5% and 1% of the storage proteins of the seed.

8. A seed, according to claim 7, wherein said seed is a legume, a cereal, or tobacco.

9. A seed according to claim 8, wherein said seed is from rice, maize, hard or soft wheat, oats, spelt, barley, soybean, pea, bean, or tobacco.

10. A method for production of the genetically transformed plant according to claim 1, said method comprising:
   i) transforming plant cells using a strain of *Agrobacterium*, said strain comprising one or more expression vectors, wherein said expression vector(s) encode(s) at least one mutein of human lipoprotein (Apo) A-1 comprising at least two residues mutated to cysteine, each of which forms a disulfide bridge to a different monomer, thereby forming oligomers;
   ii) selecting the cells in which successful transformation with said expression vector(s) has been verified; and
   iii) using said cells for regeneration of said transformed plant.

11. A method for production of the seed according to claim 5, comprising:
   i) transforming plant cells using a strain of *Agrobacterium*, said strain comprising one or more expression vectors, wherein said expression vector(s) encode(s) at least one mutein of human lipoprotein (Apo) A-1 comprising at least two residues mutated to cysteine, each of which forms a disulfide bridge to a different monomer, thereby forming oligomers;
   ii) selecting the cells in which successful transformation with said expression vector(s) has been verified;
   iii) using said cells for regeneration of said transformed plant capable of producing said seeds; and
   iv) growing said transformed plant to maturity to produce seeds.

12. The method according to claim 11, wherein said seed is a legume, a cereal, or tobacco.

13. A method of extraction and purification from the seed according to claim 5 of one or more muteins of human apolipoprotein (Apo) A-1 in an essentially oligomeric form, wherein the oligomeric form comprises three or more monomers, wherein said one or more muteins are characterised in that they show in their oligomeric forms biological activities equal to or higher than the activities shown by apolipoprotein (Apo) A-1 Milano in its dimeric form in the following tests:
   a') measurement of reverse cholesterol transport capacity evaluated by calculation of association kinetics of equal quantities of said oligomer, and of said dimer of Apo A-1 Milano with dimyristoylphosphatidylcholine (DMPC);
   b') measurement of plasma half life of said oligomer by a plasma half life test in comparison to a calibration curve obtained performing the same test with the purified Apo A-1 Milano dimer;
   the method comprising:
   a) grinding said seed in liquid nitrogen in the presence of an extraction buffer;
   b) centrifuging the solution obtained in a) at 14,000 g for 15 min at 4° C. to obtain a supernatant;
   c) subjecting the supernatant to several chromatographic steps comprising exclusion chromatography and ion exchange chromatography to obtain partially purified oligomeric protein; and
   d) further purifying the partially purified oligomeric protein by HPLC.

14. A product comprising the oligomeric human apolipoprotein (Apo) A-1 mutein(s) obtainable by the method according to claim 13.

15. The method according to claim 13, wherein said oligomer is a heteromer, the method further comprising:
   e) diluting the oligomeric mutein obtained in c) or d) in buffer with a reducing agent;
   f) gel filtering a suspension of e) and recovering monomers;
   g) repeating from a) to e) for further different seeds producing one or more muteins that are different from the one or more muteins already purified in monomeric form;
   h) admixing the different monomers produced from a) to f) in stoichiometric ratios in oxidising conditions and/or in the presence of the enzyme disulfite isomerase; and
   i) collecting the heteromers obtained in h).

16. A product obtainable with the method according to claim 15.

17. A method of using the seed according to claim 5, wherein one or more muteins of human apolipoprotein (Apo) A-1 are in an essentially oligomeric form, wherein the oligomeric form comprises three of more monomers, said one or more muteins characterized in that they show in their oligomeric forms biological activities equal to or higher than the activities shown by apolipoprotein (Apo) A-1 Milano in its dimeric form in the following tests:
   a') measurement of reverse cholesterol transport capacity evaluated by calculation of association kinetics of equal quantities of said oligomer, and of said dimer of Apo A-1 Milano with dimyristoylphosphatidylcholine (DMPC); and
   b') measurement of plasma half life of said oligomer by a plasma half life test in comparison to a calibration curve obtained performing the same test with the purified Apo A-1 Milano dimer;
   wherein said one or more muteins are purified from said seeds and mixed with pharmaceutically acceptable excipients to prepare a medicament.

18. A method of using the seed according to claim 5, wherein said one or more muteins in oligomeric form from said seed are administered to a patient in need thereof to increase the level of HDL cholesterol in the patient's blood plasma.

19. A method of using the seed according to claim 5, for preparation of a food and/or nutraceutical containing one or more muteins of human apolipoprotein (Apo) A-1 in an essentially oligomeric form, wherein the oligomeric form comprises three or more monomers, said one or more muteins characterized in that they show in the oligomeric forms biological activities equal to or higher than the activities shown by apolipoprotein (Apo) A-1 Milano in its dimeric form in the following tests:
   a') measurement of reverse cholesterol transport capacity evaluated by calculation of association kinetics of equal quantities of said oligomer, and of the dimer of Apo A-1 Milano with dimyristoylphosphatidylcholine (DMPC);
   b') measurement of plasma half life of said oligomer by a plasma half life test in comparison to a calibration curve obtained performing the same test with the purified Apo A-1 Milano dimer;

the method comprising: harvesting, preserving, and aliquoting said seed in cases suitable for selling or combining said seed with suitable food excipients and subsequently aliquoting in cases suitable for selling.

20. A nutraceutical containing one or more muteins of human apolipoprotein (Apo) A-1 in an essentially oligomeric form, wherein the oligomeric form comprises three or more monomers, said one or more muteins characterized in that they show in the oligomeric forms biological activities equal to or higher than the activities shown by apolipoprotein (Apo) A-1 Milano in its dimeric form in the following tests:

a') measurement of reverse cholesterol transport capacity evaluated by calculation of association kinetics of equal quantities of said oligomer, and of the dimer of Apo A-1 Milano with dimyristoylphosphatidylcholine (DMPC);

b') measurement of plasma half life of said oligomer by a plasma half life test in comparison to a calibration curve obtained performing the same test with the purified Apo A-1 Milano dimer;

comprising muteins derived from the seeds according to claim 13.

21. A nutraceutical according to claim 20, wherein said nutraceutical is in the form of a dried or puffed cereal, a food product, a plant milk or derivative thereof, flour, a pastry product, a pasta product, or a fresh legume or derivative thereof.

22. A method of using the seed according to claim 5, for storage and/or preservation of one or more muteins of human apolipoprotein (Apo) A-1 in an essentially oligomeric form, wherein the oligomeric form comprises three or more monomers, wherein said one or more muteins are characterised in that they show in their oligomeric forms biological activities equal to or higher than the activities shown by apolipoprotein (Apo) A-1 Milano in its dimeric form in the following tests:

a') measurement of reverse cholesterol transport capacity evaluated by calculation of association kinetics of equal quantities of said oligomer, and of the said dimer of Apo A-1 Milano with dimyristoylphosphatidylcholine (DMPC); and b') measurement of plasma half life of said oligomer by a plasma half life test in comparison to a calibration curve obtained performing the same test with the purified Apo A-1 Milano dimer;

the method comprising: storing and/or preserving said one or more muteins in the form of seed.

23. A method for production of heteromers of muteins of human apolipoprotein (Apo) A-1 in an essentially oligomeric form, wherein the oligomeric form comprises three or more monomers, wherein said muteins are characterised in that they show in their oligomeric forms biological activities equal to or higher than activities shown by apolipoprotein (Apo) A-1 Milano in its dimeric form in the following tests:

a') measurement of reverse cholesterol transport capacity evaluated by calculation of association kinetics of equal quantities of said oligomer, and of the said dimer of Apo A-1 Milano with dimyristoylphosphatidylcholine (DMPC); and b') measurement of plasma half life of said oligomer by a plasma half life test in comparison to a calibration curve obtained performing the same test with the purified Apo A-1 Milano dimer;

the method comprising:

a) crossbreeding one or more times plants according to claim 9, wherein said produced muteins are different from plant to plant; and b) selecting the plants expressing at least two of said different muteins.

* * * * *

SEQUENCE LISTING

```
<160> NUMBER OF SEQ ID NOS: 56

<210> SEQ ID NO 1
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of Human Apo A-1  R173C: Apo A-1 Milano

<400> SEQUENCE: 1 gat gaa ccc ccc cag agc ccc tgg gat cga gtg aag gac ctg gcc act       48
Asp Glu Pro Pro Gln Ser Pro Trp Asp Arg Val Lys Asp Leu Ala Thr
1               5                  10                  15 gtg tac gtg gat gtg ctc aaa gac agc ggc aga gac tat gtg tcc cag       96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac      144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc      192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag      240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag      288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg      336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag      384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg      432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc      480
Gly Glu Glu Met Arg Asp Arg Ala Arg Ala His Val Asp Ala Leu Arg
145                 150                 155                 160 acg cat ctg gcc ccc tac agc gac gag ctg cgc cag tgc ttg gcc gcg      528
Thr His Leu Ala Pro Tyr Ser Asp Glu Leu Arg Gln Cys Leu Ala Ala
                165                 170                 175 cgc ctt gag gct ctc aag gag aac ggc ggc gcc aga ctg gcc gag tac      576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag      624
His Ala Lys Ala Thr Glu His Leu Ser Thr Leu Ser Glu Lys Ala Lys
        195                 200                 205
```

```
ccc gcg ctc gag gac ctc cgc caa ggc ctg ctg ccc gtg ctg gag agc      672
Pro Ala Leu Glu Asp Leu Arg Gln Gly Leu Leu Pro Val Leu Glu Ser
    210             215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225             230                 235                 240 aac acc cag tga                                                      732
Asn Thr Gln <210> SEQ ID NO 2
<211> LENGTH: 243
<212> TYPE: PRT
<213> ORGANISM: Homo sapiens

<400> SEQUENCE: 2

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 3
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R123C

<400> SEQUENCE: 3 gat gaa ccc ccc cag agc ccc tgg gat cga gtg aag gac ctg gcc act      48
```

```
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag     288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg tgc gca gag ctc caa gag     384
Glu Leu Tyr Arg Gln Lys Val Glu Pro Leu Cys Ala Glu Leu Gln Glu
        115                 120                 125 ggc gcg cgc cag aag ctg cac gag ctg caa gag aag ctg agc cca ctg     432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc     480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg     528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac     576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag     624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc     672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc     720
Phe Lys Val Ser Phe Leu Ser Ala Leu Glu Glu Tyr Thr Lys Lys Leu
225                 230                 235                 240 aac acc cag tga                                                     732
Asn Thr Gln <210> SEQ ID NO 4
<211> LENGTH: 243
<212> TYPE: PRT
<213> ORGANISM: Homo sapiens

<400> SEQUENCE: 4

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45
```

```
Asn Trp Asp Ser Val Thr Ser Thr Phe Ser Lys Leu Arg Glu Gln Leu
     50                  55                  60
Gly Pro Val Thr Gln Glu Phe Trp Asp Asn Leu Glu Lys Glu Thr Glu
 65                  70                  75                  80
Gly Leu Arg Gln Glu Met Ser Lys Asp Leu Glu Glu Val Lys Ala Lys
                 85                  90                  95
Val Gln Pro Tyr Leu Asp Asp Phe Gln Lys Lys Trp Gln Glu Glu Met
             100                 105                 110
Glu Leu Tyr Arg Gln Lys Val Glu Pro Leu Cys Ala Glu Leu Gln Glu
         115                 120                 125
Gly Ala Arg Gln Lys Leu His Glu Leu Gln Glu Lys Leu Ser Pro Leu
130                 135                 140
Gly Glu Glu Met Arg Asp Arg Ala Arg Ala His Val Asp Ala Leu Arg
145                 150                 155                 160
Thr His Leu Ala Pro Tyr Ser Asp Glu Leu Arg Gln Arg Leu Ala Ala
                165                 170                 175
Arg Leu Glu Ala Leu Lys Glu Asn Gly Gly Ala Arg Leu Ala Glu Tyr
            180                 185                 190
His Ala Lys Ala Thr Glu His Leu Ser Thr Leu Ser Glu Lys Ala Lys
        195                 200                 205
Pro Ala Leu Glu Asp Leu Arg Gln Gly Leu Leu Pro Val Leu Glu Ser
    210                 215                 220
Phe Lys Val Ser Phe Leu Ser Ala Leu Glu Glu Tyr Thr Lys Lys Leu
225                 230                 235                 240
Asn Thr Gln

<210> SEQ ID NO 5
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R215C

<400> SEQUENCE: 5 gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
 1               5                  10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
             20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
         35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
 50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
 65                  70                  75                  80 ggc ctg agg caa gag atg agc aag gat ctg gag gag gtg aag gcc aag     288
Gly Leu Arg Gln Glu Met Ser Lys Asp Leu Glu Glu Val Lys Ala Lys
                 85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
```

```
Glu Leu Tyr Arg Gln Lys Val Glu Pro Leu Arg Ala Glu Leu Gln Glu
            115                 120                 125 ggc gcg cgc cag aag ctg cac gag ctg caa gag aag ctg agc cca ctg      432
Gly Ala Arg Gln Lys Leu His Glu Leu Gln Glu Lys Leu Ser Pro Leu
130                 135                 140 ggc gag gag atg cgc gac cgc gcg cgc gcc cat gtg gac gcg ctg cgc      480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg      528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac      576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag      624
His Ala Lys Ala Thr Glu His Leu Ser Thr Leu Ser Glu Lys Ala Lys
        195                 200                 205 ccc gcg ctc gag gac ctc tgc caa ggc ctg ctg ccc gtg ctg gag agc      672
Pro Ala Leu Glu Asp Leu Cys Gln Gly Leu Leu Pro Val Leu Glu Ser
210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                      732
Asn Thr Gln <210> SEQ ID NO 6
<211> LENGTH: 243
<212> TYPE: PRT
<213> ORGANISM: Homo sapiens

<400> SEQUENCE: 6

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
```

```
                195                 200                 205
Pro Ala Leu Glu Asp Leu Cys Gln Gly Leu Leu Pro Val Leu Glu Ser
            210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 7
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R173C, R215C

<400> SEQUENCE: 7 gat gaa ccc ccc cag agc ccc tgg gat cga gtg aag gac ctg gcc act    48
Asp Glu Pro Pro Gln Ser Pro Trp Asp Arg Val Lys Asp Leu Ala Thr
1               5                  10                  15 gtg tac gtg gat gtg ctc aaa gac agc ggc aga gac tat gtg tcc cag    96
Val Tyr Val Asp Val Leu Lys Asp Ser Gly Arg Asp Tyr Val Ser Gln
                20                  25                  30 ttt gaa ggc tcc gcc ttg gga aaa cag cta aac cta aag ctc ctt gac   144
Phe Glu Gly Ser Ala Leu Gly Lys Gln Leu Asn Leu Lys Leu Leu Asp
            35                  40                  45 aac tgg gac agc gtg acc tcc acc ttc agc aag ctg cgc gaa cag ctc   192
Asn Trp Asp Ser Val Thr Ser Thr Phe Ser Lys Leu Arg Glu Gln Leu
        50                  55                  60 ggc cct gtg acc cag gag ttc tgg gat aac ctg gaa aag gag aca gag   240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag   288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg   336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag   384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg   432
Gly Ala Arg Gln Lys Leu His Glu Leu Gln Glu Lys Leu Ser Pro Leu
130                 135                 140 ggc gag gag atg cgc gac cgc gcg cgc gcc cat gtg gac gcg ctg cgc   480
Gly Glu Glu Met Arg Asp Arg Ala Arg Ala His Val Asp Ala Leu Arg
145                 150                 155                 160 acg cat ctg gcc ccc tac agc gac gag ctg cgc cag tgc ttg gcc gcg   528
Thr His Leu Ala Pro Tyr Ser Asp Glu Leu Arg Gln Cys Leu Ala Ala
            165                 170                 175 cgc ctt gag gct ctc aag gag aac ggc ggc gcc aga ctg gcc gag tac   576
Arg Leu Glu Ala Leu Lys Glu Asn Gly Gly Ala Arg Leu Ala Glu Tyr
        180                 185                 190 cac gcc aag gcc acc gag cat ctg agc acg ctc agc gag aag gcc aag   624
His Ala Lys Ala Thr Glu His Leu Ser Thr Leu Ser Glu Lys Ala Lys
            195                 200                 205 ccc gcg ctc gag gac ctc tgc caa ggc ctg ctg ccc gtg ctg gag agc   672
Pro Ala Leu Glu Asp Leu Cys Gln Gly Leu Leu Pro Val Leu Glu Ser
210                 215                 220 ttc aag gtc agc ttc ctg agc gct ctc gag gag tac act aag aag ctc   720
```

```
Phe Lys Val Ser Phe Leu Ser Ala Leu Glu Glu Tyr Thr Lys Lys Leu
225                 230                 235                 240 aac acc cag tga                                                          732
Asn Thr Gln
```

<210> SEQ ID NO 8
<211> LENGTH: 243
<212> TYPE: PRT
<213> ORGANISM: Homo sapiens

<400> SEQUENCE: 8

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
        50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln
```

<210> SEQ ID NO 9
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R123C, R215C

<400> SEQUENCE: 9

```
gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
```

```
                   20                  25                  30
ttt gaa ggc tcc gcc ttg gga aaa cag cta aac cta aag ctc ctt gac    144
Phe Glu Gly Ser Ala Leu Gly Lys Gln Leu Asn Leu Lys Leu Leu Asp
         35                  40                  45 aac tgg gac agc gtg acc tcc acc ttc agc aag ctg cgc gaa cag ctc    192
Asn Trp Asp Ser Val Thr Ser Thr Phe Ser Lys Leu Arg Glu Gln Leu
 50                  55                  60 ggc cct gtg acc cag gag ttc tgg gat aac ctg gaa aag gag aca gag    240
Gly Pro Val Thr Gln Glu Phe Trp Asp Asn Leu Glu Lys Glu Thr Glu
 65                  70                  75                  80 ggc ctg agg caa gag atg agc aag gat ctg gag gag gtg aag gcc aag    288
Gly Leu Arg Gln Glu Met Ser Lys Asp Leu Glu Glu Val Lys Ala Lys
             85                  90                  95 gtg cag ccc tac ctg gac gac ttc cag aag aag tgg cag gag gag atg    336
Val Gln Pro Tyr Leu Asp Asp Phe Gln Lys Lys Trp Gln Glu Glu Met
            100                 105                 110 gag ctc tac cgc cag aag gtg gag ccg ctg tgc gca gag ctc caa gag    384
Glu Leu Tyr Arg Gln Lys Val Glu Pro Leu Cys Ala Glu Leu Gln Glu
            115                 120                 125 ggc gcg cgc cag aag ctg cac gag ctg caa gag aag ctg agc cca ctg    432
Gly Ala Arg Gln Lys Leu His Glu Leu Gln Glu Lys Leu Ser Pro Leu
        130                 135                 140 ggc gag gag atg cgc gac cgc gcg cgc gcc cat gtg gac gcg ctg cgc    480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg    528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac    576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag    624
His Ala Lys Ala Thr Glu His Leu Ser Thr Leu Ser Glu Lys Ala Lys
            195                 200                 205 ccc gcg ctc gag gac ctc tgc caa ggc ctg ctg ccc gtg ctg gag agc    672
Pro Ala Leu Glu Asp Leu Cys Gln Gly Leu Leu Pro Val Leu Glu Ser
        210                 215                 220 ttc aag gtc agc ttc ctg agc gct ctc gag gag tac act aag aag ctc    720
Phe Lys Val Ser Phe Leu Ser Ala Leu Glu Glu Tyr Thr Lys Lys Leu
225                 230                 235                 240 aac acc cag tga                                                    732
Asn Thr Gln <210> SEQ ID NO 10
<211> LENGTH: 243
<212> TYPE: PRT
<213> ORGANISM: Homo sapiens

<400> SEQUENCE: 10

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
        50                  55                  60

Gly Pro Val Thr Gln Glu Phe Trp Asp Asn Leu Glu Lys Glu Thr Glu
 65                  70                  75                  80
```

```
Gly Leu Arg Gln Glu Met Ser Lys Asp Leu Glu Glu Val Lys Ala Lys
                 85                  90                  95
Val Gln Pro Tyr Leu Asp Asp Phe Gln Lys Lys Trp Gln Glu Glu Met
                100                 105                 110
Glu Leu Tyr Arg Gln Lys Val Glu Pro Leu Cys Ala Glu Leu Gln Glu
            115                 120                 125
Gly Ala Arg Gln Lys Leu His Glu Leu Gln Glu Lys Leu Ser Pro Leu
        130                 135                 140
Gly Glu Glu Met Arg Asp Arg Ala Arg Ala His Val Asp Ala Leu Arg
145                 150                 155                 160
Thr His Leu Ala Pro Tyr Ser Asp Glu Leu Arg Gln Arg Leu Ala Ala
                165                 170                 175
Arg Leu Glu Ala Leu Lys Glu Asn Gly Gly Ala Arg Leu Ala Glu Tyr
                180                 185                 190
His Ala Lys Ala Thr Glu His Leu Ser Thr Leu Ser Glu Lys Ala Lys
            195                 200                 205
Pro Ala Leu Glu Asp Leu Cys Gln Gly Leu Leu Pro Val Leu Glu Ser
        210                 215                 220
Phe Lys Val Ser Phe Leu Ser Ala Leu Glu Glu Tyr Thr Lys Lys Leu
225                 230                 235                 240
Asn Thr Gln

<210> SEQ ID NO 11
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R10C

<400> SEQUENCE: 11
```

| | | | | | | | | | | | | | | | | |
|---|---|---|---|---|---|---|---|---|---|---|---|---|---|---|---|---|
| gat | gaa | ccc | ccc | cag | agc | ccc | tgg | gat | tgt | gtg | aag | gac | ctg | gcc | act | 48 |
| Asp | Glu | Pro | Pro | Gln | Ser | Pro | Trp | Asp | Cys | Val | Lys | Asp | Leu | Ala | Thr | |
| 1 | | | | 5 | | | | | 10 | | | | | 15 | | |
| gtg | tac | gtg | gat | gtg | ctc | aaa | gac | agc | ggc | aga | gac | tat | gtg | tcc | cag | 96 |
| Val | Tyr | Val | Asp | Val | Leu | Lys | Asp | Ser | Gly | Arg | Asp | Tyr | Val | Ser | Gln | |
| | | | 20 | | | | | 25 | | | | | 30 | | | |
| ttt | gaa | ggc | tcc | gcc | ttg | gga | aaa | cag | cta | aac | cta | aag | ctc | ctt | gac | 144 |
| Phe | Glu | Gly | Ser | Ala | Leu | Gly | Lys | Gln | Leu | Asn | Leu | Lys | Leu | Leu | Asp | |
| | | 35 | | | | | 40 | | | | | 45 | | | | |
| aac | tgg | gac | agc | gtg | acc | tcc | acc | ttc | agc | aag | ctg | cgc | gaa | cag | ctc | 192 |
| Asn | Trp | Asp | Ser | Val | Thr | Ser | Thr | Phe | Ser | Lys | Leu | Arg | Glu | Gln | Leu | |
| | 50 | | | | | 55 | | | | | 60 | | | | | |
| ggc | cct | gtg | acc | cag | gag | ttc | tgg | gat | aac | ctg | gaa | aag | gag | aca | gag | 240 |
| Gly | Pro | Val | Thr | Gln | Glu | Phe | Trp | Asp | Asn | Leu | Glu | Lys | Glu | Thr | Glu | |
| 65 | | | | | 70 | | | | | 75 | | | | | 80 | |
| ggc | ctg | agg | caa | gag | atg | agc | aag | gat | ctg | gag | gag | gtg | aag | gcc | aag | 288 |
| Gly | Leu | Arg | Gln | Glu | Met | Ser | Lys | Asp | Leu | Glu | Glu | Val | Lys | Ala | Lys | |
| | | | | 85 | | | | | 90 | | | | | 95 | | |
| gtg | cag | ccc | tac | ctg | gac | gac | ttc | cag | aag | aag | tgg | cag | gag | gag | atg | 336 |
| Val | Gln | Pro | Tyr | Leu | Asp | Asp | Phe | Gln | Lys | Lys | Trp | Gln | Glu | Glu | Met | |
| | | | 100 | | | | | 105 | | | | | 110 | | | |
| gag | ctc | tac | cgc | cag | aag | gtg | gag | ccg | ctg | cgc | gca | gag | ctc | caa | gag | 384 |
| Glu | Leu | Tyr | Arg | Gln | Lys | Val | Glu | Pro | Leu | Arg | Ala | Glu | Leu | Gln | Glu | |
| | | 115 | | | | | 120 | | | | | 125 | | | | |
| ggc | gcg | cgc | cag | aag | ctg | cac | gag | ctg | caa | gag | aag | ctg | agc | cca | ctg | 432 |
| Gly | Ala | Arg | Gln | Lys | Leu | His | Glu | Leu | Gln | Glu | Lys | Leu | Ser | Pro | Leu | |

```
ggc gag gag atg cgc gac cgc gcg cgc gcc cat gtg gac gcg ctg cgc      480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg      528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac      576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag      624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc      672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                       732
Asn Thr Gln
```

<210> SEQ ID NO 12
<211> LENGTH: 243
<212> TYPE: PRT
<213> ORGANISM: Homo sapiens

<400> SEQUENCE: 12

```
Asp Glu Pro Pro Gln Ser Pro Trp Asp Cys Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220
```

Phe Lys Val Ser Phe Leu Ser Ala Leu Glu Glu Tyr Thr Lys Lys Leu
                225                 230                 235                 240

Asn Thr Gln

<210> SEQ ID NO 13
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R61C

<400> SEQUENCE: 13

```
gat gaa ccc ccc cag agc ccc tgg gat cga gtg aag gac ctg gcc act        48
Asp Glu Pro Pro Gln Ser Pro Trp Asp Arg Val Lys Asp Leu Ala Thr
1               5                   10                  15 gtg tac gtg gat gtg ctc aaa gac agc gga aga gac tat gtg tcc cag        96
Val Tyr Val Asp Val Leu Lys Asp Ser Gly Arg Asp Tyr Val Ser Gln
                20                  25                  30 ttt gaa ggc tcc gcc ttg gga aaa cag cta aac cta aag ctc ctt gac       144
Phe Glu Gly Ser Ala Leu Gly Lys Gln Leu Asn Leu Lys Leu Leu Asp
            35                  40                  45 aac tgg gac agc gtg acc tcc acc ttc agc aag ctg tgc gaa cag ctc       192
Asn Trp Asp Ser Val Thr Ser Thr Phe Ser Lys Leu Cys Glu Gln Leu
        50                  55                  60 ggc cct gtg acc cag gag ttc tgg gat aac ctg gaa aag gag aca gag       240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag       288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg       336
Val Gln Pro Tyr Leu Asp Asp Phe Gln Lys Lys Trp Gln Glu Glu Met
                100                 105                 110 gag ctc tac cgc cag aag gtg gag ccg ctg cgc gca gag ctc caa gag       384
Glu Leu Tyr Arg Gln Lys Val Glu Pro Leu Arg Ala Glu Leu Gln Glu
            115                 120                 125 ggc gcg cgc cag aag ctg cac gag ctg caa gag aag ctg agc cca ctg       432
Gly Ala Arg Gln Lys Leu His Glu Leu Gln Glu Lys Leu Ser Pro Leu
        130                 135                 140 ggc gag gag atg cgc gac cgc gcg cgc gcc cat gtg gac gcg ctg cgc       480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg       528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac       576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag       624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc       672
Pro Ala Leu Glu Asp Leu Arg Gln Gly Leu Leu Pro Val Leu Glu Ser
210                 215                 220 ttc aag gtc agc ttc ctg agc gct ctc gag gag tac act aag aag ctc       720
Phe Lys Val Ser Phe Leu Ser Ala Leu Glu Glu Tyr Thr Lys Lys Leu
225                 230                 235                 240 aac acc cag tga                                                        732
Asn Thr Gln
```

<210> SEQ ID NO 14
<211> LENGTH: 243
<212> TYPE: PRT
<213> ORGANISM: Homo sapiens

<400> SEQUENCE: 14

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Cys Glu Gln Leu
50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 15
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R83C

<400> SEQUENCE: 15 gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
        35                  40                  45

```
aac tgg gac agc gtg acc tcc acc ttc agc aag ctg cgc gaa cag ctc      192
Asn Trp Asp Ser Val Thr Ser Thr Phe Ser Lys Leu Arg Glu Gln Leu
 50                  55                  60 ggc cct gtg acc cag gag ttc tgg gat aac ctg gaa aag gag aca gag      240
Gly Pro Val Thr Gln Glu Phe Trp Asp Asn Leu Glu Lys Glu Thr Glu
 65                  70                  75                  80 ggc ctg tgc caa gag atg agc aag gat ctg gag gag gtg aag gcc aag      288
Gly Leu Cys Gln Glu Met Ser Lys Asp Leu Glu Glu Val Lys Ala Lys
                     85                  90                  95 gtg cag ccc tac ctg gac gac ttc cag aag aag tgg cag gag gag atg      336
Val Gln Pro Tyr Leu Asp Asp Phe Gln Lys Lys Trp Gln Glu Glu Met
                    100                 105                 110 gag ctc tac cgc cag aag gtg gag ccg ctg cgc gca gag ctc caa gag      384
Glu Leu Tyr Arg Gln Lys Val Glu Pro Leu Arg Ala Glu Leu Gln Glu
                115                 120                 125 ggc gcg cgc cag aag ctg cac gag ctg caa gag aag ctg agc cca ctg      432
Gly Ala Arg Gln Lys Leu His Glu Leu Gln Glu Lys Leu Ser Pro Leu
130                 135                 140 ggc gag gag atg cgc gac cgc gcg cgc gcc cat gtg gac gcg ctg cgc      480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg      528
Thr His Leu Ala Pro Tyr Ser Asp Glu Leu Arg Gln Arg Leu Ala Ala
                    165                 170                 175 cgc ctt gag gct ctc aag gag aac ggc ggc gcc aga ctg gcc gag tac      576
Arg Leu Glu Ala Leu Lys Glu Asn Gly Gly Ala Arg Leu Ala Glu Tyr
                180                 185                 190 cac gcc aag gcc acc gag cat ctg agc acg ctc agc gag aag gcc aag      624
His Ala Lys Ala Thr Glu His Leu Ser Thr Leu Ser Glu Lys Ala Lys
            195                 200                 205 ccc gcg ctc gag gac ctc cgc caa ggc ctg ctg ccc gtg ctg gag agc      672
Pro Ala Leu Glu Asp Leu Arg Gln Gly Leu Leu Pro Val Leu Glu Ser
210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                      732
Asn Thr Gln <210> SEQ ID NO 16
<211> LENGTH: 243
<212> TYPE: PRT
<213> ORGANISM: Homo sapiens

<400> SEQUENCE: 16

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu
 65                  70                  75                  80

Gly Leu Cys Gln Glu Met Ser Lys Asp Leu Glu Glu Val Lys Ala Lys
                     85                  90                  95

Val Gln Pro Tyr Leu Asp Asp Phe Gln Lys Lys Trp Gln Glu Glu Met
```

```
              100                 105                 110
Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 17
<211> LENGTH: 732
<212> TYPE: DNA
<213> ORGANISM: Homo sapiens
<220> FEATURE:
<221> NAME/KEY: CDS
<222> LOCATION: (1)..(723)
<223> OTHER INFORMATION: Mutein of human Apo A-1 R151C

<400> SEQUENCE: 17 gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                  10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag     288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg     432
Gly Ala Arg Gln Lys Leu His Glu Leu Gln Glu Lys Leu Ser Pro Leu
    130                 135                 140 ggc gag gag atg cgc gac tgc gcg cgc gcc cat gtg gac gcg ctg cgc     480
Gly Glu Glu Met Arg Asp Cys Ala Arg Ala His Val Asp Ala Leu Arg
145                 150                 155                 160
```

| | | | | | | | | | | | | | | | |
|---|---|---|---|---|---|---|---|---|---|---|---|---|---|---|---|
| acg | cat | ctg | gcc | ccc | tac | agc | gac | gag | ctg | cgc | cag | cgc | ttg | gcc | gcg | 528 |
| Thr | His | Leu | Ala | Pro | Tyr | Ser | Asp | Glu | Leu | Arg | Gln | Arg | Leu | Ala | Ala | |
| | | | 165 | | | | | 170 | | | | | 175 | | | |

| cgc | ctt | gag | gct | ctc | aag | gag | aac | ggc | ggc | gcc | aga | ctg | gcc | gag | tac | 576 |
| Arg | Leu | Glu | Ala | Leu | Lys | Glu | Asn | Gly | Gly | Ala | Arg | Leu | Ala | Glu | Tyr | |
| | | 180 | | | | | 185 | | | | | 190 | | | | |

| cac | gcc | aag | gcc | acc | gag | cat | ctg | agc | acg | ctc | agc | gag | aag | gcc | aag | 624 |
| His | Ala | Lys | Ala | Thr | Glu | His | Leu | Ser | Thr | Leu | Ser | Glu | Lys | Ala | Lys | |
| | | 195 | | | | | 200 | | | | | 205 | | | | |

| ccc | gcg | ctc | gag | gac | ctc | cgc | caa | ggc | ctg | ctg | ccc | gtg | ctg | gag | agc | 672 |
| Pro | Ala | Leu | Glu | Asp | Leu | Arg | Gln | Gly | Leu | Leu | Pro | Val | Leu | Glu | Ser | |
| | 210 | | | | | 215 | | | | | 220 | | | | | |

| ttc | aag | gtc | agc | ttc | ctg | agc | gct | ctc | gag | gag | tac | act | aag | aag | ctc | 720 |
| Phe | Lys | Val | Ser | Phe | Leu | Ser | Ala | Leu | Glu | Glu | Tyr | Thr | Lys | Lys | Leu | |
| 225 | | | | | 230 | | | | | 235 | | | | | 240 | |

| aac | acccagtga | | | | | | | | | | | | | | | 732 |
| Asn | | | | | | | | | | | | | | | | |

<210> SEQ ID NO 18
<211> LENGTH: 241
<212> TYPE: PRT
<213> ORGANISM: Homo sapiens

<400> SEQUENCE: 18

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn

<210> SEQ ID NO 19
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R10C, R215C

<400> SEQUENCE: 19

| | | | | | | | | | | | | | | | | |
|---|---|---|---|---|---|---|---|---|---|---|---|---|---|---|---|---|
| gat | gaa | ccc | ccc | cag | agc | ccc | tgg | gat | tgt | gtg | aag | gac | ctg | gcc | act | 48 |
| Asp | Glu | Pro | Pro | Gln | Ser | Pro | Trp | Asp | Cys | Val | Lys | Asp | Leu | Ala | Thr | |
| 1 | | | | 5 | | | | | 10 | | | | | 15 | | |

| gtg | tac | gtg | gat | gtg | ctc | aaa | gac | agc | ggc | aga | gac | tat | gtg | tcc | cag | 96 |
|---|---|---|---|---|---|---|---|---|---|---|---|---|---|---|---|---|
| Val | Tyr | Val | Asp | Val | Leu | Lys | Asp | Ser | Gly | Arg | Asp | Tyr | Val | Ser | Gln | |
| | | | 20 | | | | | 25 | | | | | 30 | | | |

| ttt | gaa | ggc | tcc | gcc | ttg | gga | aaa | cag | cta | aac | cta | aag | ctc | ctt | gac | 144 |
|---|---|---|---|---|---|---|---|---|---|---|---|---|---|---|---|---|
| Phe | Glu | Gly | Ser | Ala | Leu | Gly | Lys | Gln | Leu | Asn | Leu | Lys | Leu | Leu | Asp | |
| | | 35 | | | | | 40 | | | | | 45 | | | | |

| aac | tgg | gac | agc | gtg | acc | tcc | acc | ttc | agc | aag | ctg | cgc | gaa | cag | ctc | 192 |
|---|---|---|---|---|---|---|---|---|---|---|---|---|---|---|---|---|
| Asn | Trp | Asp | Ser | Val | Thr | Ser | Thr | Phe | Ser | Lys | Leu | Arg | Glu | Gln | Leu | |
| 50 | | | | | 55 | | | | | 60 | | | | | | |

| ggc | cct | gtg | acc | cag | gag | ttc | tgg | gat | aac | ctg | gaa | aag | gag | aca | gag | 240 |
|---|---|---|---|---|---|---|---|---|---|---|---|---|---|---|---|---|
| Gly | Pro | Val | Thr | Gln | Glu | Phe | Trp | Asp | Asn | Leu | Glu | Lys | Glu | Thr | Glu | |
| 65 | | | | 70 | | | | | 75 | | | | | 80 | | |

| ggc | ctg | agg | caa | gag | atg | agc | aag | gat | ctg | gag | gag | gtg | aag | gcc | aag | 288 |
|---|---|---|---|---|---|---|---|---|---|---|---|---|---|---|---|---|
| Gly | Leu | Arg | Gln | Glu | Met | Ser | Lys | Asp | Leu | Glu | Glu | Val | Lys | Ala | Lys | |
| | | | | 85 | | | | | 90 | | | | | 95 | | |

| gtg | cag | ccc | tac | ctg | gac | gac | ttc | cag | aag | aag | tgg | cag | gag | gag | atg | 336 |
|---|---|---|---|---|---|---|---|---|---|---|---|---|---|---|---|---|
| Val | Gln | Pro | Tyr | Leu | Asp | Asp | Phe | Gln | Lys | Lys | Trp | Gln | Glu | Glu | Met | |
| | | | 100 | | | | | 105 | | | | | 110 | | | |

| gag | ctc | tac | cgc | cag | aag | gtg | gag | ccg | ctg | cgc | gca | gag | ctc | caa | gag | 384 |
|---|---|---|---|---|---|---|---|---|---|---|---|---|---|---|---|---|
| Glu | Leu | Tyr | Arg | Gln | Lys | Val | Glu | Pro | Leu | Arg | Ala | Glu | Leu | Gln | Glu | |
| | | 115 | | | | | 120 | | | | | 125 | | | | |

| ggc | gcg | cgc | cag | aag | ctg | cac | gag | ctg | caa | gag | aag | ctg | agc | cca | ctg | 432 |
|---|---|---|---|---|---|---|---|---|---|---|---|---|---|---|---|---|
| Gly | Ala | Arg | Gln | Lys | Leu | His | Glu | Leu | Gln | Glu | Lys | Leu | Ser | Pro | Leu | |
| | | 130 | | | | | 135 | | | | | 140 | | | | |

| ggc | gag | gag | atg | cgc | gac | cgc | gcg | cgc | gcc | cat | gtg | gac | gcg | ctg | cgc | 480 |
|---|---|---|---|---|---|---|---|---|---|---|---|---|---|---|---|---|
| Gly | Glu | Glu | Met | Arg | Asp | Arg | Ala | Arg | Ala | His | Val | Asp | Ala | Leu | Arg | |
| 145 | | | | | 150 | | | | | 155 | | | | | 160 | |

| acg | cat | ctg | gcc | ccc | tac | agc | gac | gag | ctg | cgc | cag | cgc | ttg | gcc | gcg | 528 |
|---|---|---|---|---|---|---|---|---|---|---|---|---|---|---|---|---|
| Thr | His | Leu | Ala | Pro | Tyr | Ser | Asp | Glu | Leu | Arg | Gln | Arg | Leu | Ala | Ala | |
| | | | | 165 | | | | | 170 | | | | | 175 | | |

| cgc | ctt | gag | gct | ctc | aag | gag | aac | ggc | ggc | gcc | aga | ctg | gcc | gag | tac | 576 |
|---|---|---|---|---|---|---|---|---|---|---|---|---|---|---|---|---|
| Arg | Leu | Glu | Ala | Leu | Lys | Glu | Asn | Gly | Gly | Ala | Arg | Leu | Ala | Glu | Tyr | |
| | | | 180 | | | | | 185 | | | | | 190 | | | |

| cac | gcc | aag | gcc | acc | gag | cat | ctg | agc | acg | ctc | agc | gag | aag | gcc | aag | 624 |
|---|---|---|---|---|---|---|---|---|---|---|---|---|---|---|---|---|
| His | Ala | Lys | Ala | Thr | Glu | His | Leu | Ser | Thr | Leu | Ser | Glu | Lys | Ala | Lys | |
| | | 195 | | | | | 200 | | | | | 205 | | | | |

| ccc | gcg | ctc | gag | gac | ctc | tgc | caa | ggc | ctg | ctg | ccc | gtg | ctg | gag | agc | 672 |
|---|---|---|---|---|---|---|---|---|---|---|---|---|---|---|---|---|
| Pro | Ala | Leu | Glu | Asp | Leu | Cys | Gln | Gly | Leu | Leu | Pro | Val | Leu | Glu | Ser | |
| | | 210 | | | | | 215 | | | | | 220 | | | | |

| ttc | aag | gtc | agc | ttc | ctg | agc | gct | ctc | gag | gag | tac | act | aag | aag | ctc | 720 |
|---|---|---|---|---|---|---|---|---|---|---|---|---|---|---|---|---|
| Phe | Lys | Val | Ser | Phe | Leu | Ser | Ala | Leu | Glu | Glu | Tyr | Thr | Lys | Lys | Leu | |
| 225 | | | | | 230 | | | | | 235 | | | | | 240 | |

| aac | acc | cag | tga | | | | | | | | | | | | | 732 |
|---|---|---|---|---|---|---|---|---|---|---|---|---|---|---|---|---|
| Asn | Thr | Gln | | | | | | | | | | | | | | |

<210> SEQ ID NO 20
<211> LENGTH: 243
<212> TYPE: PRT

<213> ORGANISM: Homo sapiens

<400> SEQUENCE: 20

Asp Glu Pro Pro Gln Ser Pro Trp Asp Cys Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 21
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R61C, R173C

<400> SEQUENCE: 21 gat gaa ccc ccc cag agc ccc tgg gat cga gtg aag gac ctg gcc act        48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag        96
Val Tyr Val Asp Val Leu Lys Asp Ser Gly Arg Asp Tyr Val Ser Gln
                20                  25                  30 ttt gaa ggc tcc gcc ttg gga aaa cag cta aac cta aag ctc ctt gac       144
Phe Glu Gly Ser Ala Leu Gly Lys Gln Leu Asn Leu Lys Leu Leu Asp
            35                  40                  45 aac tgg gac agc gtg acc tcc acc ttc agc aag ctg tgc gaa cag ctc       192
Asn Trp Asp Ser Val Thr Ser Thr Phe Ser Lys Leu Cys Glu Gln Leu
    50                  55                  60

```
ggc cct gtg acc cag gag ttc tgg gat aac ctg gaa aag gag aca gag      240
Gly Pro Val Thr Gln Glu Phe Trp Asp Asn Leu Glu Lys Glu Thr Glu
 65                  70                  75                  80 ggc ctg agg caa gag atg agc aag gat ctg gag gag gtg aag gcc aag      288
Gly Leu Arg Gln Glu Met Ser Lys Asp Leu Glu Glu Val Lys Ala Lys
                 85                  90                  95 gtg cag ccc tac ctg gac gac ttc cag aag aag tgg cag gag gag atg      336
Val Gln Pro Tyr Leu Asp Asp Phe Gln Lys Lys Trp Gln Glu Glu Met
             100                 105                 110 gag ctc tac cgc cag aag gtg gag ccg ctg cgc gca gag ctc caa gag      384
Glu Leu Tyr Arg Gln Lys Val Glu Pro Leu Arg Ala Glu Leu Gln Glu
         115                 120                 125 ggc gcg cgc cag aag ctg cac gag ctg caa gag aag ctg agc cca ctg      432
Gly Ala Arg Gln Lys Leu His Glu Leu Gln Glu Lys Leu Ser Pro Leu
     130                 135                 140 ggc gag gag atg cgc gac cgc gcg cgc gcc cat gtg gac gcg ctg cgc      480
Gly Glu Glu Met Arg Asp Arg Ala Arg Ala His Val Asp Ala Leu Arg
 145                 150                 155                 160 acg cat ctg gcc ccc tac agc gac gag ctg cgc cag tgc ttg gcc gcg      528
Thr His Leu Ala Pro Tyr Ser Asp Glu Leu Arg Gln Cys Leu Ala Ala
                 165                 170                 175 cgc ctt gag gct ctc aag gag aac ggc ggc gcc aga ctg gcc gag tac      576
Arg Leu Glu Ala Leu Lys Glu Asn Gly Gly Ala Arg Leu Ala Glu Tyr
             180                 185                 190 cac gcc aag gcc acc gag cat ctg agc acg ctc agc gag aag gcc aag      624
His Ala Lys Ala Thr Glu His Leu Ser Thr Leu Ser Glu Lys Ala Lys
         195                 200                 205 ccc gcg ctc gag gac ctc cgc caa ggc ctg ctg ccc gtg ctg gag agc      672
Pro Ala Leu Glu Asp Leu Arg Gln Gly Leu Leu Pro Val Leu Glu Ser
     210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
 225                 230                 235                 240 aac acc cag tga                                                      732
Asn Thr Gln <210> SEQ ID NO 22
<211> LENGTH: 243
<212> TYPE: PRT
<213> ORGANISM: Homo sapiens

<400> SEQUENCE: 22

Asp Glu Pro Pro Gln Ser Pro Trp Asp Arg Val Lys Asp Leu Ala Thr
  1               5                  10                  15

Val Tyr Val Asp Val Leu Lys Asp Ser Gly Arg Asp Tyr Val Ser Gln
                 20                  25                  30

Phe Glu Gly Ser Ala Leu Gly Lys Gln Leu Asn Leu Lys Leu Leu Asp
             35                  40                  45

Asn Trp Asp Ser Val Thr Ser Thr Phe Ser Lys Leu Cys Glu Gln Leu
 50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                 85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125
```

```
Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 23
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R61C, R215C

<400> SEQUENCE: 23 gat gaa ccc ccc cag agc ccc tgg gat cga gtg aag gac ctg gcc act    48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag    96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac   144
Phe Glu Gly Ser Ala Leu Gly Lys Gln Leu Asn Leu Lys Leu Leu Asp
        35                  40                  45 aac tgg gac agc gtg acc tcc acc ttc agc aag ctg tgc gaa cag ctc   192
Asn Trp Asp Ser Val Thr Ser Thr Phe Ser Lys Leu Cys Glu Gln Leu
    50                  55                  60 ggc cct gtg acc cag gag ttc tgg gat aac ctg gaa aag gag aca gag   240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag   288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg   336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag   384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg   432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc   480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg   528
Thr His Leu Ala Pro Tyr Ser Asp Glu Leu Arg Gln Arg Leu Ala Ala
                165                 170                 175
```

```
cgc ctt gag gct ctc aag gag aac ggc ggc gcc aga ctg gcc gag tac    576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag    624
His Ala Lys Ala Thr Glu His Leu Ser Thr Leu Ser Glu Lys Ala Lys
        195                 200                 205 ccc gcg ctc gag gac ctc tgc caa ggc ctg ctg ccc gtg ctg gag agc    672
Pro Ala Leu Glu Asp Leu Cys Gln Gly Leu Leu Pro Val Leu Glu Ser
    210                 215                 220 ttc aag gtc agc ttc ctg agc gct ctc gag gag tac act aag aag ctc    720
Phe Lys Val Ser Phe Leu Ser Ala Leu Glu Glu Tyr Thr Lys Lys Leu
225                 230                 235                 240 aac acc cag tga                                                     732
Asn Thr Gln <210> SEQ ID NO 24
<211> LENGTH: 243
<212> TYPE: PRT
<213> ORGANISM: Homo sapiens

<400> SEQUENCE: 24

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Cys Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 25
<211> LENGTH: 732
<212> TYPE: DNA
<213> ORGANISM: Homo sapiens
```

<220> FEATURE:
<221> NAME/KEY: CDS
<222> LOCATION: (1)..(732)
<223> OTHER INFORMATION: Mutein of human Apo A-1 R61C, R151C

<400> SEQUENCE: 25

```
gat gaa ccc ccc cag agc ccc tgg gat cga gtg aag gac ctg gcc act        48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag        96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac       144
Phe Glu Gly Ser Ala Leu Gly Lys Gln Leu Asn Leu Lys Leu Leu Asp
        35                  40                  45 aac tgg gac agc gtg acc tcc acc ttc agc aag ctg tgc gaa cag ctc       192
Asn Trp Asp Ser Val Thr Ser Thr Phe Ser Lys Leu Cys Glu Gln Leu
50                  55                  60 ggc cct gtg acc cag gag ttc tgg gat aac ctg gaa aag gag aca gag       240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag       288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg       336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag       384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg       432
Gly Ala Arg Gln Lys Leu His Glu Leu Gln Glu Lys Leu Ser Pro Leu
130                 135                 140 ggc gag gag atg cgc gac tgc gcg cgc gcc cat gtg gac gcg ctg cgc       480
Gly Glu Glu Met Arg Asp Cys Ala Arg Ala His Val Asp Ala Leu Arg
145                 150                 155                 160 acg cat ctg gcc ccc tac agc gac gag ctg cgc cag cgc ttg gcc gcg       528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac       576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag       624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc       672
Pro Ala Leu Glu Asp Leu Arg Gln Gly Leu Leu Pro Val Leu Glu Ser
210                 215                 220 ttc aag gtc agc ttc ctg agc gct ctc gag gag tac act aag aag ctc       720
Phe Lys Val Ser Phe Leu Ser Ala Leu Glu Glu Tyr Thr Lys Lys Leu
225                 230                 235                 240 aac acc cag tga                                                        732
Asn Thr Gln
```

<210> SEQ ID NO 26
<211> LENGTH: 243
<212> TYPE: PRT
<213> ORGANISM: Homo sapiens

<400> SEQUENCE: 26

Asp Glu Pro Pro Gln Ser Pro Trp Asp Arg Val Lys Asp Leu Ala Thr

```
                1               5                  10                 15
              Val Tyr Val Asp Val Leu Lys Asp Ser Gly Arg Asp Tyr Val Ser Gln
                           20                  25                  30

Phe Glu Gly Ser Ala Leu Gly Lys Gln Leu Asn Leu Lys Leu Leu Asp
                           35                  40                  45

Asn Trp Asp Ser Val Thr Ser Thr Phe Ser Lys Leu Cys Glu Gln Leu
                   50                  55                  60

Gly Pro Val Thr Gln Glu Phe Trp Asp Asn Leu Glu Lys Glu Thr Glu
              65                  70                  75                  80

Gly Leu Arg Gln Glu Met Ser Lys Asp Leu Glu Glu Val Lys Ala Lys
                                85                  90                  95

Val Gln Pro Tyr Leu Asp Asp Phe Gln Lys Lys Trp Gln Glu Glu Met
                          100                 105                 110

Glu Leu Tyr Arg Gln Lys Val Glu Pro Leu Arg Ala Glu Leu Gln Glu
                          115                 120                 125

Gly Ala Arg Gln Lys Leu His Glu Leu Gln Glu Lys Leu Ser Pro Leu
                          130                 135                 140

Gly Glu Glu Met Arg Asp Cys Ala Arg Ala His Val Asp Ala Leu Arg
              145                 150                 155                 160

Thr His Leu Ala Pro Tyr Ser Asp Glu Leu Arg Gln Arg Leu Ala Ala
                                165                 170                 175

Arg Leu Glu Ala Leu Lys Glu Asn Gly Gly Ala Arg Leu Ala Glu Tyr
                          180                 185                 190

His Ala Lys Ala Thr Glu His Leu Ser Thr Leu Ser Glu Lys Ala Lys
                          195                 200                 205

Pro Ala Leu Glu Asp Leu Arg Gln Gly Leu Leu Pro Val Leu Glu Ser
                          210                 215                 220

Phe Lys Val Ser Phe Leu Ser Ala Leu Glu Glu Tyr Thr Lys Lys Leu
              225                 230                 235                 240

Asn Thr Gln

<210> SEQ ID NO 27
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R83C, R173C

<400> SEQUENCE: 27 gat gaa ccc ccc cag agc ccc tgg gat cga gtg aag gac ctg gcc act       48
Asp Glu Pro Pro Gln Ser Pro Trp Asp Arg Val Lys Asp Leu Ala Thr
1               5                  10                  15 gtg tac gtg gat gtg ctc aaa gac agc ggc aga gac tat gtg tcc cag       96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac      144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc      192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag      240
Gly Pro Val Thr Gln Glu Phe Trp Asp Asn Leu Glu Lys Glu Thr Glu
65                  70                  75                  80 ggc ctg tgc caa gag atg agc aag gat ctg gag gag gtg aag gcc aag      288
```

```
Gly Leu Cys Gln Glu Met Ser Lys Asp Leu Glu Glu Val Lys Ala Lys
                85                  90                  95 gtg cag ccc tac ctg gac gac ttc cag aag aag tgg cag gag gag atg      336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag      384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg      432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc      480
Gly Glu Glu Met Arg Asp Arg Ala Arg Ala His Val Asp Ala Leu Arg
145                 150                 155                 160 acg cat ctg gcc ccc tac agc gac gag ctg cgc cag tgc ttg gcc gcg      528
Thr His Leu Ala Pro Tyr Ser Asp Glu Leu Arg Gln Cys Leu Ala Ala
                165                 170                 175 cgc ctt gag gct ctc aag gag aac ggc ggc gcc aga ctg gcc gag tac      576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag      624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc      672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                       732
Asn Thr Gln <210> SEQ ID NO 28
<211> LENGTH: 243
<212> TYPE: PRT
<213> ORGANISM: Homo sapiens

<400> SEQUENCE: 28

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Cys Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160
```

```
Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln
```

<210> SEQ ID NO 29
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R83C, R151C

<400> SEQUENCE: 29

```
gat gaa ccc ccc cag agc ccc tgg gat cga gtg aag gac ctg gcc act     48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag     96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac    144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc    192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag    240
Gly Pro Val Thr Gln Glu Phe Trp Asp Asn Leu Glu Lys Glu Thr Glu
65                  70                  75                  80 ggc ctg tgc caa gag atg agc aag gat ctg gag gag gtg aag gcc aag    288
Gly Leu Cys Gln Glu Met Ser Lys Asp Leu Glu Glu Val Lys Ala Lys
                85                  90                  95 gtg cag ccc tac ctg gac gac ttc cag aag aag tgg cag gag gag atg    336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag    384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg    432
Gly Ala Arg Gln Lys Leu His Glu Leu Gln Glu Lys Leu Ser Pro Leu
    130                 135                 140 ggc gag gag atg cgc gac tgc gcg cgc gcc cat gtg gac gcg ctg cgc    480
Gly Glu Glu Met Arg Asp Cys Ala Arg Ala His Val Asp Ala Leu Arg
145                 150                 155                 160 acg cat ctg gcc ccc tac agc gac gag ctg cgc cag cgc ttg gcc gcg    528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac    576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag    624
His Ala Lys Ala Thr Glu His Leu Ser Thr Leu Ser Glu Lys Ala Lys
```

```
His Ala Lys Ala Thr Glu His Leu Ser Thr Leu Ser Glu Lys Ala Lys
            195                 200                 205 ccc gcg ctc gag gac ctc cgc caa ggc ctg ctg ccc gtg ctg gag agc      672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                       732
Asn Thr Gln <210> SEQ ID NO 30
<211> LENGTH: 243
<212> TYPE: PRT
<213> ORGANISM: Homo sapiens

<400> SEQUENCE: 30

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Cys Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 31
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R83C, R215C
```

<400> SEQUENCE: 31

```
gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
65                  70                  75                  80 ggc ctg tgc caa gag atg agc aag gat ctg gag gag gtg aag gcc aag     288
Gly Leu Cys Gln Glu Met Ser Lys Asp Leu Glu Glu Val Lys Ala Lys
                85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg     432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc     480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg     528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac     576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag     624
His Ala Lys Ala Thr Glu His Leu Ser Thr Leu Ser Glu Lys Ala Lys
        195                 200                 205 ccc gcg ctc gag gac ctc tgc caa ggc ctg ctg ccc gtg ctg gag agc     672
Pro Ala Leu Glu Asp Leu Cys Gln Gly Leu Leu Pro Val Leu Glu Ser
    210                 215                 220 ttc aag gtc agc ttc ctg agc gct ctc gag gag tac act aag aag ctc     720
Phe Lys Val Ser Phe Leu Ser Ala Leu Glu Glu Tyr Thr Lys Lys Leu
225                 230                 235                 240 aac acc cag tga                                                     732
Asn Thr Gln
```

<210> SEQ ID NO 32
<211> LENGTH: 243
<212> TYPE: PRT
<213> ORGANISM: Homo sapiens

<400> SEQUENCE: 32

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30
```

-continued

```
Phe Glu Gly Ser Ala Leu Gly Lys Gln Leu Asn Leu Lys Leu Leu Asp
         35                  40                  45

Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu
 65                  70                  75                  80

Gly Leu Cys Gln Glu Met Ser Lys Asp Leu Glu Glu Val Lys Ala Lys
                 85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln
```

<210> SEQ ID NO 33
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R151C, R173C

<400> SEQUENCE: 33

```
gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
 1               5                  10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
 50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
 65                  70                  75                  80 ggc ctg agg caa gag atg agc aag gat ctg gag gag gtg aag gcc aag     288
Gly Leu Arg Gln Glu Met Ser Lys Asp Leu Glu Glu Val Lys Ala Lys
                 85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110
```

```
gag ctc tac cgc cag aag gtg gag ccg ctg cgc gca gag ctc caa gag    384
Glu Leu Tyr Arg Gln Lys Val Glu Pro Leu Arg Ala Glu Leu Gln Glu
            115                 120                 125 ggc gcg cgc cag aag ctg cac gag ctg caa gag aag ctg agc cca ctg    432
Gly Ala Arg Gln Lys Leu His Glu Leu Gln Glu Lys Leu Ser Pro Leu
130                 135                 140 ggc gag gag atg cgc gac tgc gcg cgc gcc cat gtg gac gcg ctg cgc    480
Gly Glu Glu Met Arg Asp Cys Ala Arg Ala His Val Asp Ala Leu Arg
145                 150                 155                 160 acg cat ctg gcc ccc tac agc gac gag ctg cgc cag tgc ttg gcc gcg    528
Thr His Leu Ala Pro Tyr Ser Asp Glu Leu Arg Gln Cys Leu Ala Ala
                165                 170                 175 cgc ctt gag gct ctc aag gag aac ggc ggc gcc aga ctg gcc gag tac    576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag    624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc    672
Pro Ala Leu Glu Asp Leu Arg Gln Gly Leu Leu Pro Val Leu Glu Ser
210                 215                 220 ttc aag gtc agc ttc ctg agc gct ctc gag gag tac act aag aag ctc    720
Phe Lys Val Ser Phe Leu Ser Ala Leu Glu Glu Tyr Thr Lys Lys Leu
225                 230                 235                 240 aac acc cag tga                                                    732
Asn Thr Gln <210> SEQ ID NO 34
<211> LENGTH: 243
<212> TYPE: PRT
<213> ORGANISM: Homo sapiens

<400> SEQUENCE: 34

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
```

```
                180                 185                 190
His Ala Lys Ala Thr Glu His Leu Ser Thr Leu Ser Glu Lys Ala Lys
            195                 200                 205

Pro Ala Leu Glu Asp Leu Arg Gln Gly Leu Leu Pro Val Leu Glu Ser
            210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 35
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R151C, R215C

<400> SEQUENCE: 35 gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                   10                  15 gtg tac gtg gat gtg ctc aaa gac agc gga aga gac tat gtg tcc cag      96
Val Tyr Val Asp Val Leu Lys Asp Ser Gly Arg Asp Tyr Val Ser Gln
                20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
            35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
        50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag     288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
                100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
            115                 120                 125 ggc gcg cgc cag aag ctg cac gag ctg caa gag aag ctg agc cca ctg     432
Gly Ala Arg Gln Lys Leu His Glu Leu Gln Glu Lys Leu Ser Pro Leu
        130                 135                 140 ggc gag gag atg cgc gac tgc gcg cgc gcc cat gtg gac gcg ctg cgc     480
Gly Glu Glu Met Arg Asp Cys Ala Arg Ala His Val Asp Ala Leu Arg
145                 150                 155                 160 acg cat ctg gcc ccc tac agc gac gag ctg cgc cag cgc ttg gcc gcg     528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac     576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag     624
His Ala Lys Ala Thr Glu His Leu Ser Thr Leu Ser Glu Lys Ala Lys
        195                 200                 205 ccc gcg ctc gag gac ctc tgc caa ggc ctg ctg ccc gtg ctg gag agc     672
Pro Ala Leu Glu Asp Leu Cys Gln Gly Leu Leu Pro Val Leu Glu Ser
```

```
                    210                 215                 220
ttc aag gtc agc ttc ctg agc gct ctc gag gag tac act aag aag ctc    720
Phe Lys Val Ser Phe Leu Ser Ala Leu Glu Glu Tyr Thr Lys Lys Leu
225                 230                 235                 240 aac acc cag tga                                                    732
Asn Thr Gln
```

<210> SEQ ID NO 36
<211> LENGTH: 243
<212> TYPE: PRT
<213> ORGANISM: Homo sapiens

<400> SEQUENCE: 36

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
        50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
                100                 105                 110

Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
        130                 135                 140

Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
        210                 215                 220

Phe Lys Val Ser Phe Leu Ser Ala Leu Glu Glu Tyr Thr Lys Lys Leu
225                 230                 235                 240

Asn Thr Gln
```

<210> SEQ ID NO 37
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Mutein of human Apo A-1 R10C, R173C

<400> SEQUENCE: 37

```
gat gaa ccc ccc cag agc ccc tgg gat tgt gtg aag gac ctg gcc act    48
Asp Glu Pro Pro Gln Ser Pro Trp Asp Cys Val Lys Asp Leu Ala Thr
1               5                   10                  15
```

| | | |
|---|---|---|
| gtg tac gtg gat gtg ctc aaa gac agc ggc aga gac tat gtg tcc cag<br>Val Tyr Val Asp Val Leu Lys Asp Ser Gly Arg Asp Tyr Val Ser Gln<br>              20                    25                  30 | 96 |
| ttt gaa ggc tcc gcc ttg gga aaa cag cta aac cta aag ctc ctt gac<br>Phe Glu Gly Ser Ala Leu Gly Lys Gln Leu Asn Leu Lys Leu Leu Asp<br>         35                    40                    45 | 144 |
| aac tgg gac agc gtg acc tcc acc ttc agc aag ctg cgc gaa cag ctc<br>Asn Trp Asp Ser Val Thr Ser Thr Phe Ser Lys Leu Arg Glu Gln Leu<br>  50                    55                    60 | 192 |
| ggc cct gtg acc cag gag ttc tgg gat aac ctg gaa aag gag aca gag<br>Gly Pro Val Thr Gln Glu Phe Trp Asp Asn Leu Glu Lys Glu Thr Glu<br>65                    70                    75                  80 | 240 |
| ggc ctg agg caa gag atg agc aag gat ctg gag gag gtg aag gcc aag<br>Gly Leu Arg Gln Glu Met Ser Lys Asp Leu Glu Glu Val Lys Ala Lys<br>                        85                    90                  95 | 288 |
| gtg cag ccc tac ctg gac gac ttc cag aag aag tgg cag gag gag atg<br>Val Gln Pro Tyr Leu Asp Asp Phe Gln Lys Lys Trp Gln Glu Glu Met<br>              100                 105                110 | 336 |
| gag ctc tac cgc cag aag gtg gag ccg ctg cgc gca gag ctc caa gag<br>Glu Leu Tyr Arg Gln Lys Val Glu Pro Leu Arg Ala Glu Leu Gln Glu<br>             115                 120                125 | 384 |
| ggc gcg cgc cag aag ctg cac gag ctg caa gag aag ctg agc cca ctg<br>Gly Ala Arg Gln Lys Leu His Glu Leu Gln Glu Lys Leu Ser Pro Leu<br>130                    135                    140 | 432 |
| ggc gag gag atg cgc gac cgc gcg cgc gcc cat gtg gac gcg ctg cgc<br>Gly Glu Glu Met Arg Asp Arg Ala Arg Ala His Val Asp Ala Leu Arg<br>145                    150                 155                160 | 480 |
| acg cat ctg gcc ccc tac agc gac gag ctg cgc cag tgc ttg gcc gcg<br>Thr His Leu Ala Pro Tyr Ser Asp Glu Leu Arg Gln Cys Leu Ala Ala<br>                 165                 170                175 | 528 |
| cgc ctt gag gct ctc aag gag aac ggc ggc gcc aga ctg gcc gag tac<br>Arg Leu Glu Ala Leu Lys Glu Asn Gly Gly Ala Arg Leu Ala Glu Tyr<br>             180                 185                190 | 576 |
| cac gcc aag gcc acc gag cat ctg agc acg ctc agc gag aag gcc aag<br>His Ala Lys Ala Thr Glu His Leu Ser Thr Leu Ser Glu Lys Ala Lys<br>                 195                 200                205 | 624 |
| ccc gcg ctc gag gac ctc cgc caa ggc ctg ctg ccc gtg ctg gag agc<br>Pro Ala Leu Glu Asp Leu Arg Gln Gly Leu Leu Pro Val Leu Glu Ser<br>210                    215                    220 | 672 |
| ttc aag gtc agc ttc ctg agc gct ctc gag gag tac act aag aag ctc<br>Phe Lys Val Ser Phe Leu Ser Ala Leu Glu Glu Tyr Thr Lys Lys Leu<br>225                    230                    235                240 | 720 |
| aac acc cag tga<br>Asn Thr Gln | 732 |

<210> SEQ ID NO 38
<211> LENGTH: 243
<212> TYPE: PRT
<213> ORGANISM: Homo sapiens

<400> SEQUENCE: 38

Asp Glu Pro Pro Gln Ser Pro Trp Asp Cys Val Lys Asp Leu Ala Thr
1                    5                    10                    15

Val Tyr Val Asp Val Leu Lys Asp Ser Gly Arg Asp Tyr Val Ser Gln
              20                    25                    30

Phe Glu Gly Ser Ala Leu Gly Lys Gln Leu Asn Leu Lys Leu Leu Asp
         35                    40                    45

Asn Trp Asp Ser Val Thr Ser Thr Phe Ser Lys Leu Arg Glu Gln Leu
  50                    55                    60

```
Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 39
<211> LENGTH: 30
<212> TYPE: DNA
<213> ORGANISM: Artificial Sequence
<220> FEATURE:
<223> OTHER INFORMATION: primer for Apo A-1 Milano of Seq ID No: 2 and
      muteins of Seq ID No: 8, 22, 28, 34, 38

<400> SEQUENCE: 39
gacgagctgc gccagtgctt ggccgcgcgc                                         30

<210> SEQ ID NO 40
<211> LENGTH: 30
<212> TYPE: DNA
<213> ORGANISM: Artificial Sequence
<220> FEATURE:
<223> OTHER INFORMATION: primer per Apo A-1 Milano of Seq ID No: 2 and
      for muteins of Seq ID No: 8, 22, 28, 34, 38

<400> SEQUENCE: 40
gcgcgcggcc aagcactggc gcagctcgtc                                         30

<210> SEQ ID NO 41
<211> LENGTH: 34
<212> TYPE: DNA
<213> ORGANISM: Artificial Sequence
<220> FEATURE:
<223> OTHER INFORMATION: primer for mutein of Seq ID No: 4, 10

<400> SEQUENCE: 41
gaaggtggag ccgctgtgcg cagagctcca agag                                    34

<210> SEQ ID NO 42
<211> LENGTH: 34
<212> TYPE: DNA
<213> ORGANISM: Artificial Sequence
```

```
<220> FEATURE:
<223> OTHER INFORMATION: primer for mutein of Seq ID No: 4, 10

<400> SEQUENCE: 42
ctcttggagc tctgcgcaca gcggctccac cttc                                    34

<210> SEQ ID NO 43
<211> LENGTH: 33
<212> TYPE: DNA
<213> ORGANISM: Artificial Sequence
<220> FEATURE:
<223> OTHER INFORMATION: primer for mutein of Seq ID No: 4, 8, 10, 20,
      24, 32, 36

<400> SEQUENCE: 43
gcgctcgagg acctctgcca aggcctgctg ccc                                     33

<210> SEQ ID NO 44
<211> LENGTH: 33
<212> TYPE: DNA
<213> ORGANISM: Artificial Sequence
<220> FEATURE:
<223> OTHER INFORMATION: primer for mutein of Seq ID No: 4, 8, 10, 20,
      24, 32, 36

<400> SEQUENCE: 44
gggcagcagg ccttggcaga ggtcctcgag cgc                                     33

<210> SEQ ID NO 45
<211> LENGTH: 27
<212> TYPE: DNA
<213> ORGANISM: Artificial Sequence
<220> FEATURE:
<223> OTHER INFORMATION: primer for mutein of seq id no: 12, 20, 38

<400> SEQUENCE: 45
agcccctggg attgtgtgaa ggacctg                                            27

<210> SEQ ID NO 46
<211> LENGTH: 27
<212> TYPE: DNA
<213> ORGANISM: Artificial Sequence
<220> FEATURE:
<223> OTHER INFORMATION: primer for mutein of Seq ID No: 12, 20, 38

<400> SEQUENCE: 46
caggtccttc acacaatccc aggggct                                            27

<210> SEQ ID NO 47
<211> LENGTH: 24
<212> TYPE: DNA
<213> ORGANISM: Artificial Sequence
<220> FEATURE:
<223> OTHER INFORMATION: primer for mutein of Seq ID No: 14, 22, 24, 26

<400> SEQUENCE: 47
ttcagcaagc tgtgcgaaca gctc                                               24

<210> SEQ ID NO 48
<211> LENGTH: 24
<212> TYPE: DNA
<213> ORGANISM: Artificial Sequence
<220> FEATURE:
<223> OTHER INFORMATION: primer for mutein of Seq ID No: 14, 22, 24, 26

<400> SEQUENCE: 48
```
gagctgttcg cacagcttgc tgaa                                        24

<210> SEQ ID NO 49
<211> LENGTH: 24
<212> TYPE: DNA
<213> ORGANISM: Artificial Sequence
<220> FEATURE:
<223> OTHER INFORMATION: primer for mutein of Seq ID No: 16, 28, 30, 32,
      34

<400> SEQUENCE: 49
acagagggcc tgtgccaaga gatg                                        24

<210> SEQ ID NO 50
<211> LENGTH: 24
<212> TYPE: DNA
<213> ORGANISM: Artificial Sequence
<220> FEATURE:
<223> OTHER INFORMATION: primer for mutein of Seq ID No: 16, 28, 30, 32,
      34

<400> SEQUENCE: 50
catctcttgg cacaggccct ctgt                                        24

<210> SEQ ID NO 51
<211> LENGTH: 24
<212> TYPE: DNA
<213> ORGANISM: Artificial Sequence
<220> FEATURE:
<223> OTHER INFORMATION: primer for mutein of Seq ID No: 18, 26, 30, 36

<400> SEQUENCE: 51
gagatgcgcg actgcgcgcg cgcc                                        24

<210> SEQ ID NO 52
<211> LENGTH: 24
<212> TYPE: DNA
<213> ORGANISM: Artificial Sequence
<220> FEATURE:
<223> OTHER INFORMATION: primer for mutein of Seq ID No: 18, 26, 30, 36

<400> SEQUENCE: 52
ggcgcgcgcg cagtcgcgca tctc                                        24

<210> SEQ ID NO 53
<211> LENGTH: 25
<212> TYPE: DNA
<213> ORGANISM: Artificial Sequence
<220> FEATURE:
<223> OTHER INFORMATION: forward primer for generation of plasmid
      pGEM-APO

<400> SEQUENCE: 53
ggatccgatg aaccccccca gagcc                                       25

<210> SEQ ID NO 54
<211> LENGTH: 28
<212> TYPE: DNA
<213> ORGANISM: Artificial Sequence
<220> FEATURE:
<223> OTHER INFORMATION: reverse primer for generation of plasmid
      pGEM-APO

<400> SEQUENCE: 54
gatatctcac tgggtgttga gcttgtag                                    28

<210> SEQ ID NO 55
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Human Apo A-1 wild type

<400> SEQUENCE: 55

```
gat gaa ccc ccc cag agc ccc tgg gat cga gtg aag gac ctg gcc act    48
Asp Glu Pro Pro Gln Ser Pro Trp Asp Arg Val Lys Asp Leu Ala Thr
 1               5                  10                  15 gtg tac gtg gat gtg ctc aaa gac agc ggc aga gac tat gtg tcc cag    96
Val Tyr Val Asp Val Leu Lys Asp Ser Gly Arg Asp Tyr Val Ser Gln
             20                  25                  30 ttt gaa ggc tcc gcc ttg gga aaa cag cta aac cta aag ctc ctt gac   144
Phe Glu Gly Ser Ala Leu Gly Lys Gln Leu Asn Leu Lys Leu Leu Asp
         35                  40                  45 aac tgg gac agc gtg acc tcc acc ttc agc aag ctg cgc gaa cag ctc   192
Asn Trp Asp Ser Val Thr Ser Thr Phe Ser Lys Leu Arg Glu Gln Leu
     50                  55                  60 ggc cct gtg acc cag gag ttc tgg gat aac ctg gaa aag gag aca gag   240
Gly Pro Val Thr Gln Glu Phe Trp Asp Asn Leu Glu Lys Glu Thr Glu
 65                  70                  75                  80 ggc ctg agg caa gag atg agc aag gat ctg gag gag gtg aag gcc aag   288
Gly Leu Arg Gln Glu Met Ser Lys Asp Leu Glu Glu Val Lys Ala Lys
                 85                  90                  95 gtg cag ccc tac ctg gac gac ttc cag aag aag tgg cag gag gag atg   336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag   384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg   432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc   480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg   528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac   576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag   624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc   672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc   720
Phe Lys Val Ser Phe Leu Ser Ala Leu Glu Glu Tyr Thr Lys Lys Leu
225                 230                 235                 240 aac acc cag tga                                                   732
Asn Thr Gln
```

<210> SEQ ID NO 56
<211> LENGTH: 243
<212> TYPE: PRT
<213> ORGANISM: Homo sapiens

```
<400> SEQUENCE: 56

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                      60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
                100                 105                 110

Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
        210                 215                 220

Phe Lys Val Ser Phe Leu Ser Ala Leu Glu Glu Tyr Thr Lys Lys Leu
225                 230                 235                 240

Asn Thr Gln
```